(12) United States Patent
Srivastava et al.

(10) Patent No.: US 7,846,436 B2
(45) Date of Patent: Dec. 7, 2010

(54) OLIGONUCLEOTIDES AND RELATED COMPOUNDS

(75) Inventors: Suresh C. Srivastava, Burlington, MA (US); Satya K. Bajpai, Burlington, MA (US); Kwok-Hung Sit, 33 Jalan Kakatua, Singapore 598552 (SG)

(73) Assignees: ChemGenes Corporation, Wilmington, MA (US); Kwok-Hung Sit, Singapore (SG)

( * ) Notice: Subject to any disclaimer, the term of this patent is extended or adjusted under 35 U.S.C. 154(b) by 874 days.

(21) Appl. No.: 10/768,996

(22) Filed: Jan. 30, 2004

(65) Prior Publication Data

US 2005/0159375 A1    Jul. 21, 2005

Related U.S. Application Data

(60) Provisional application No. 60/525,691, filed on Nov. 28, 2003.

(51) Int. Cl.
*C07H 21/02* (2006.01)
(52) U.S. Cl. .................................. 424/133.1; 536/23.1

(58) Field of Classification Search ............... 424/133.1
See application file for complete search history.

(56) References Cited

PUBLICATIONS

Weiner J. Leukocyte Biology, 2000; 68: 455-463.*
Krieg et al (Nature 1995; 374: 546-549).*
Belles et al (J. Immunology 2001; 167: 4878).*
Agrawal et al (Trends in Molecular Medicine, 2002, 8/3:114-120).*
Donnelly et al (Nature Medicine, 2003, 9/11:1354-1356).*
DeGruijl et al, Nature Medicine, 1999, 5/10:1124-1125.*
Bitton R. J. (Current Opinion in Molecular Therapeutics, 2004, 6/1:17-25).*
Freshney (Culture of Animal Cells, A Manual of Basic Technique, Alan R. Liss, Inc., 1983, New York, p. 4).*
Dermer (Bio/Technology, 1994, 12:320).*

\* cited by examiner

*Primary Examiner*—Brandon J Fetterolf
(74) *Attorney, Agent, or Firm*—Law Office of Indu M. Anand

(57) ABSTRACT

The present invention relates generally to oligonucleotides and more specifically to oligonucleotides which have a sequence including at least two CpG dinucleotides and a prodrug of an antimetabolite. The prodrug can be part of a CpG dinucleotide or may be attached elsewhere on the oligonucleotide.

40 Claims, 22 Drawing Sheets

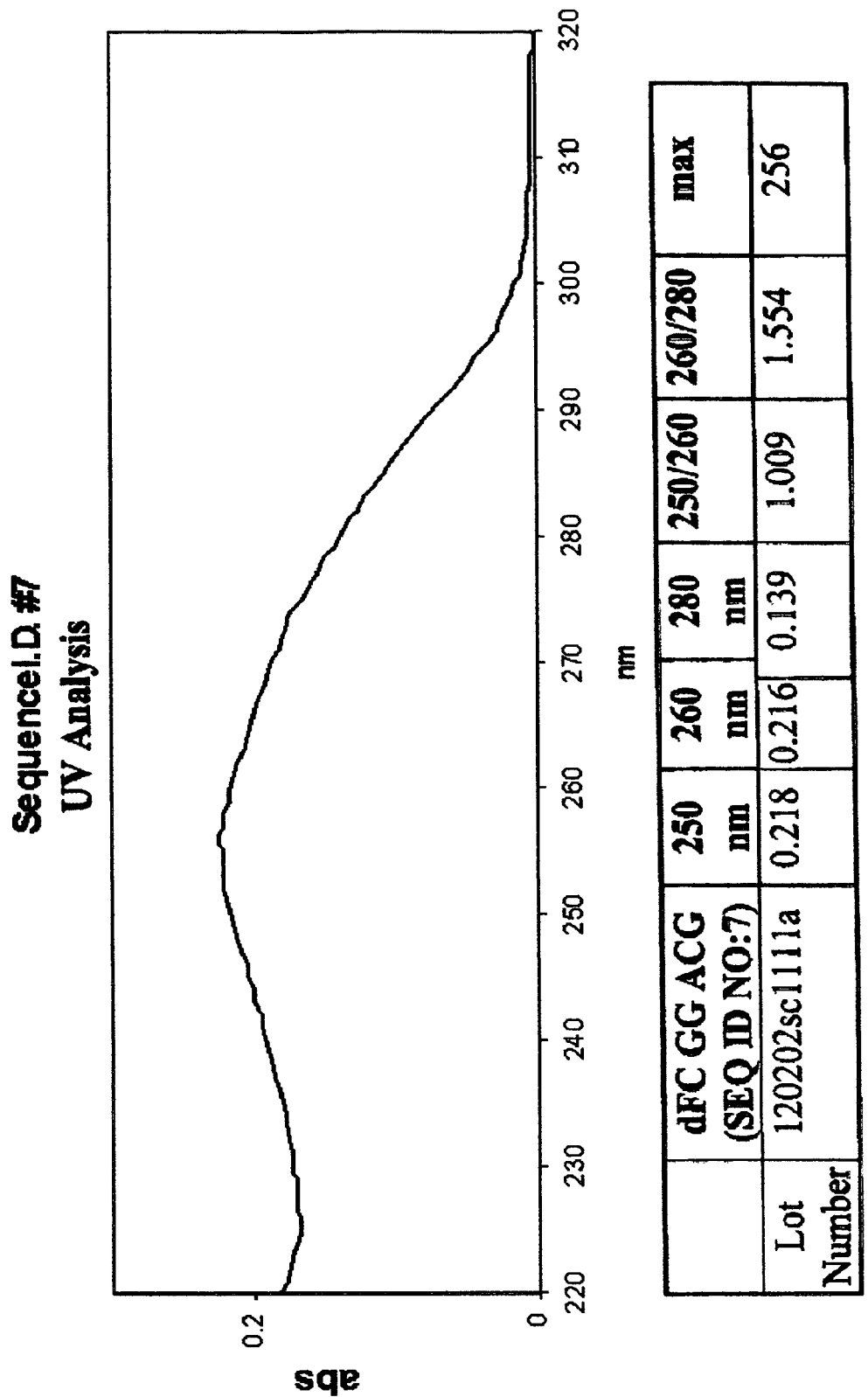
Figure 1: UV absorption spectra of oligonucleotide sequence I.D. #7. dFC GG ACG

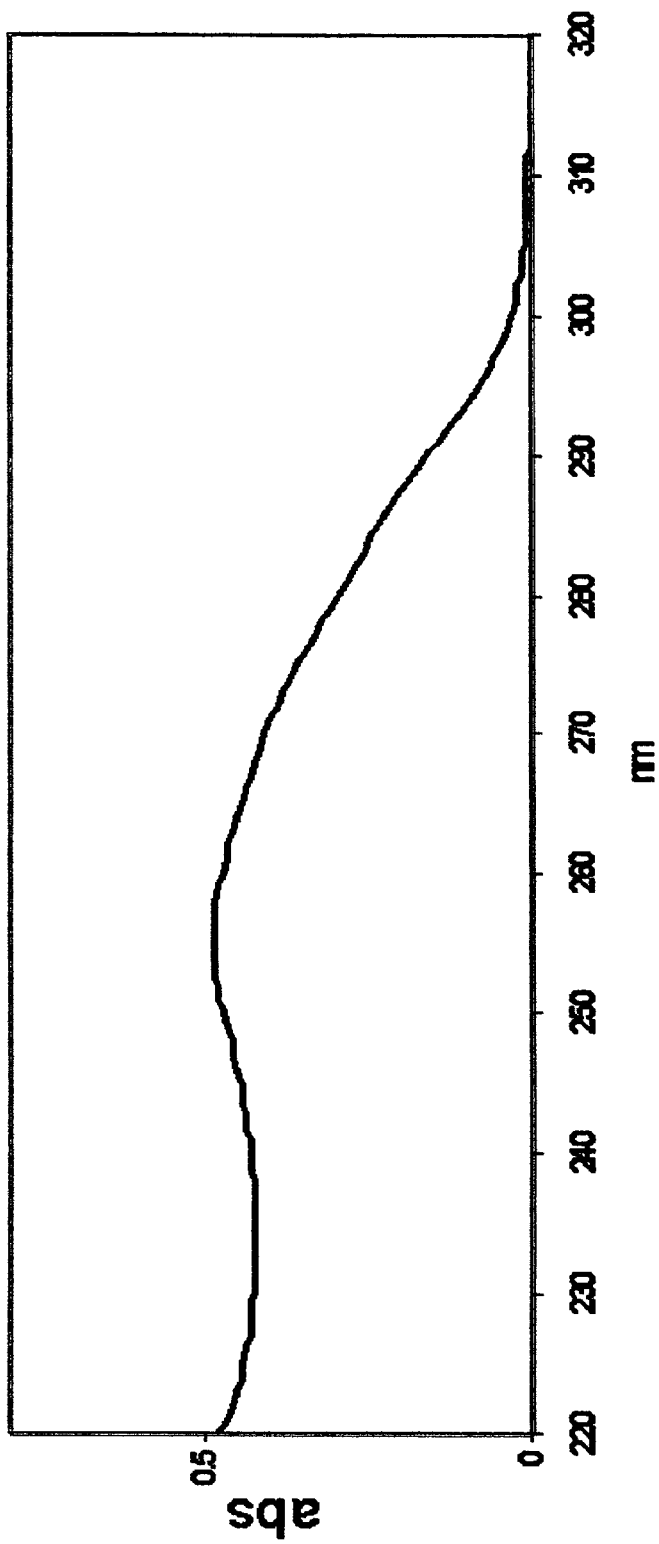
Figure 2: UV absorption spectra of oligonucleotide sequence I.D. #8. dFC GTG GAA CG

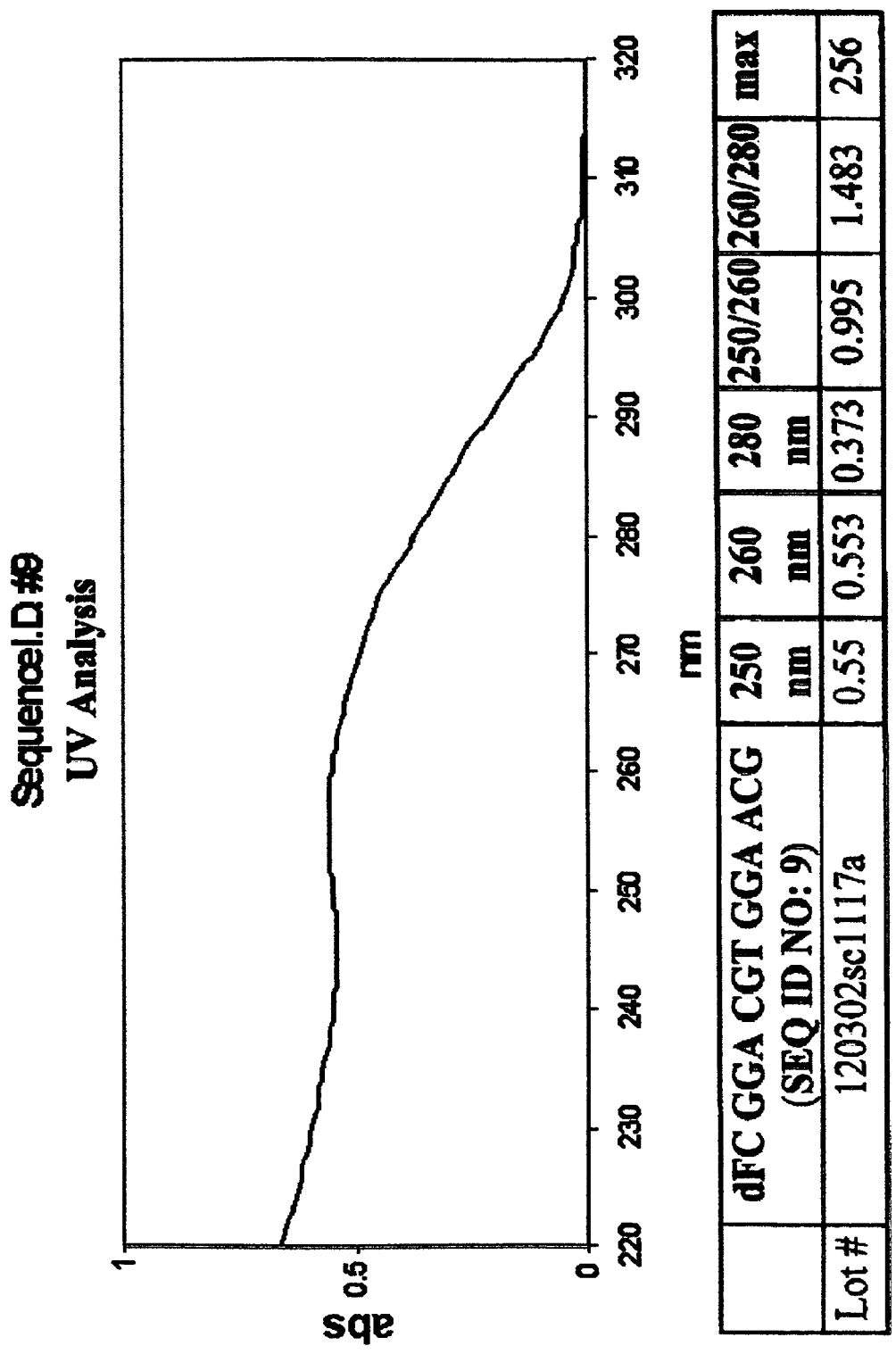
Figure 3: UV absorption spectra of oligonucleotide sequence I.D. #9. dFC GGA CGT GGA ACG.

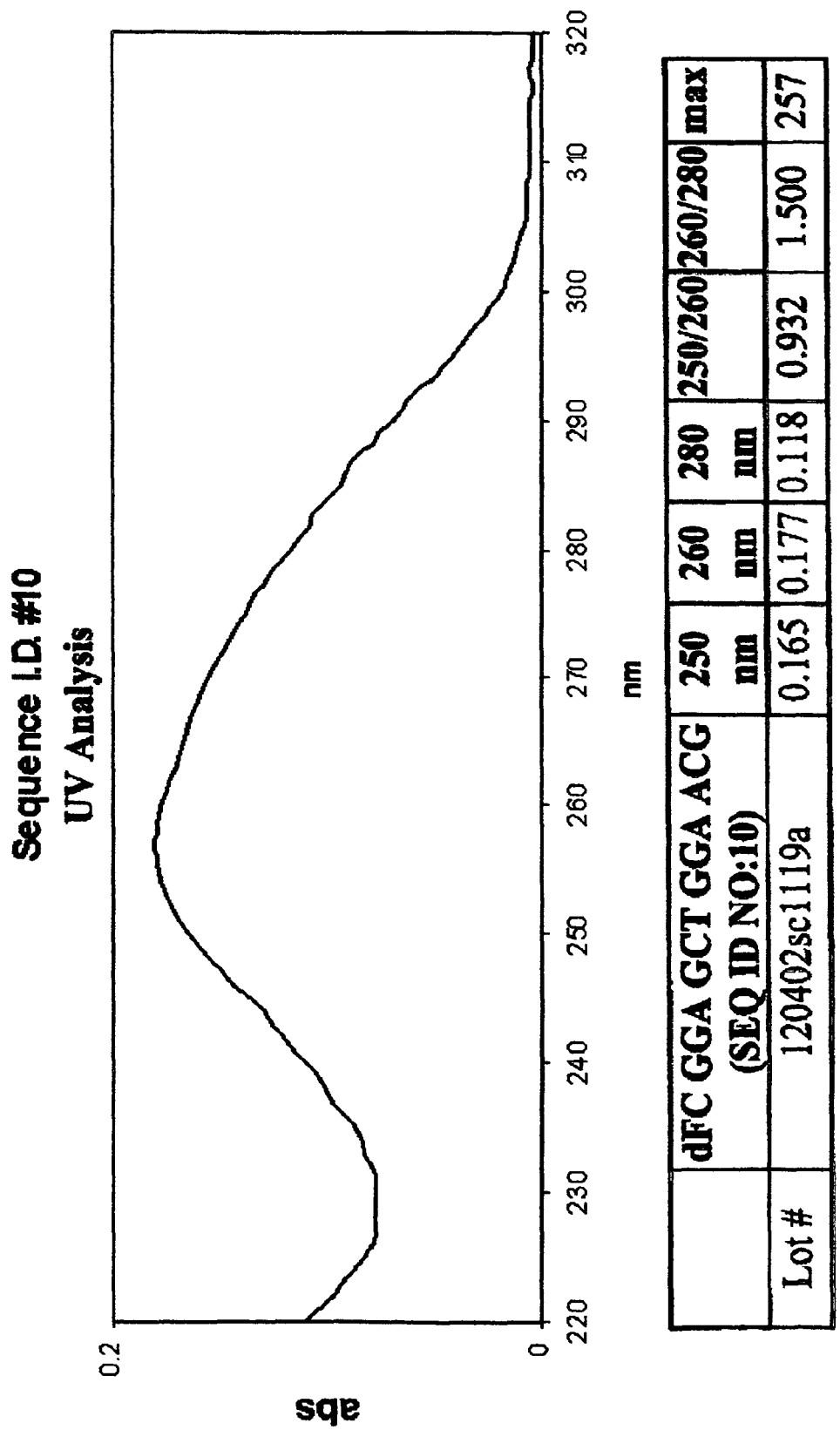
Figure 4: UV absorption spectra of oligonucleotide sequence I.D. #10. dFC GGA GCT GGA ACG.

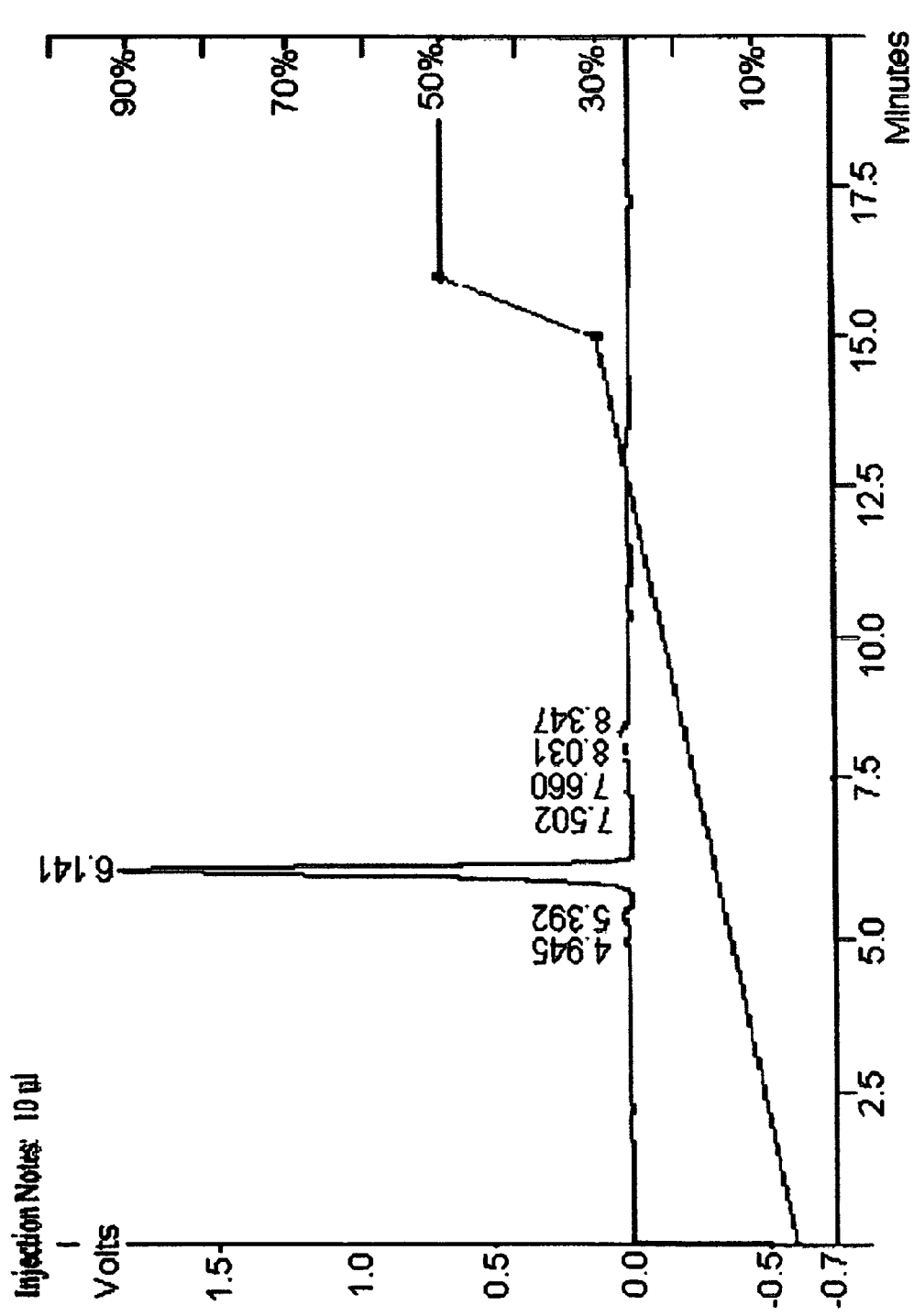
Figure 5A: HPLC analysis of the oligonucleotide sequence I.D. #7. dFC GG ACG 120202sc1111a: dFC GG ACG (SEQ ID NO: 7)

| Peak No | Ret Time(min) | Peak Name Result (%) | Peak Area (counts) | Peak Height (counts) |
|---|---|---|---|---|
| 1 | 4.945 | 0.58 | 139521 | 12576 |
| 2 | 5.392 | 2.02 | 486112 | 35915 |
| 3 | 6.141 | 90.60 | 21751388 | 1865545 |
| 4 | 7.502 | 0.85 | 204987 | 14410 |
| 5 | 7.660 | 0.68 | 162070 | 13251 |
| 6 | 8.031 | 1.64 | 394599 | 29908 |
| 7 | 8.347 | 3.62 | 869972 | 48542 |
| Totals | | 99.99 | 24008648 | 2020147 |

Figure 5B: HPLC analysis of the oligonucleotide sequence I.D. #7. dFC GG ACG

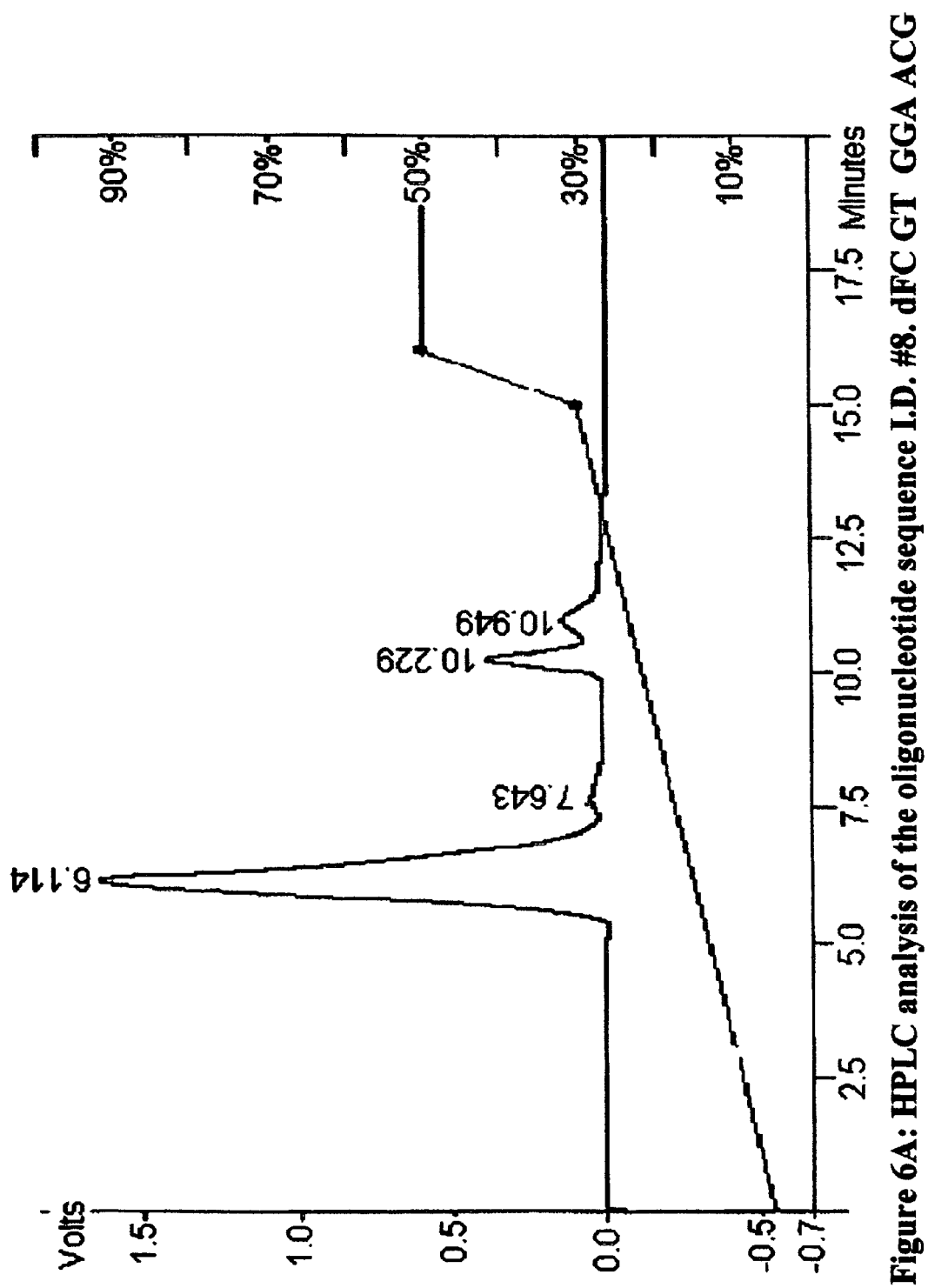
Figure 6A: HPLC analysis of the oligonucleotide sequence I.D. #8. dFC GT GGA ACG 120202sc1113a: dFC GT GGA ACG (SEQ ID NO:8)

| Peak No | Ret Time(min) | Peak Name Result (%) | Peak Area (counts) | Peak Height (counts) |
|---|---|---|---|---|
| 1 | 6.114 | 85.19 | 72523816 | 1647089 |
| 2 | 7.643 | 1.09 | 924821 | 27270 |
| 3 | 10.229 | 8.69 | 7400725 | 377325 |
| 4 | 10.949 | 5.03 | 4278076 | 125992 |
| Totals | | 100.00 | 85127440 | 2177676 |

Figure 6B: HPLC analysis of the oligonucleotide sequence I.D. #8. dFC GT GGA ACG

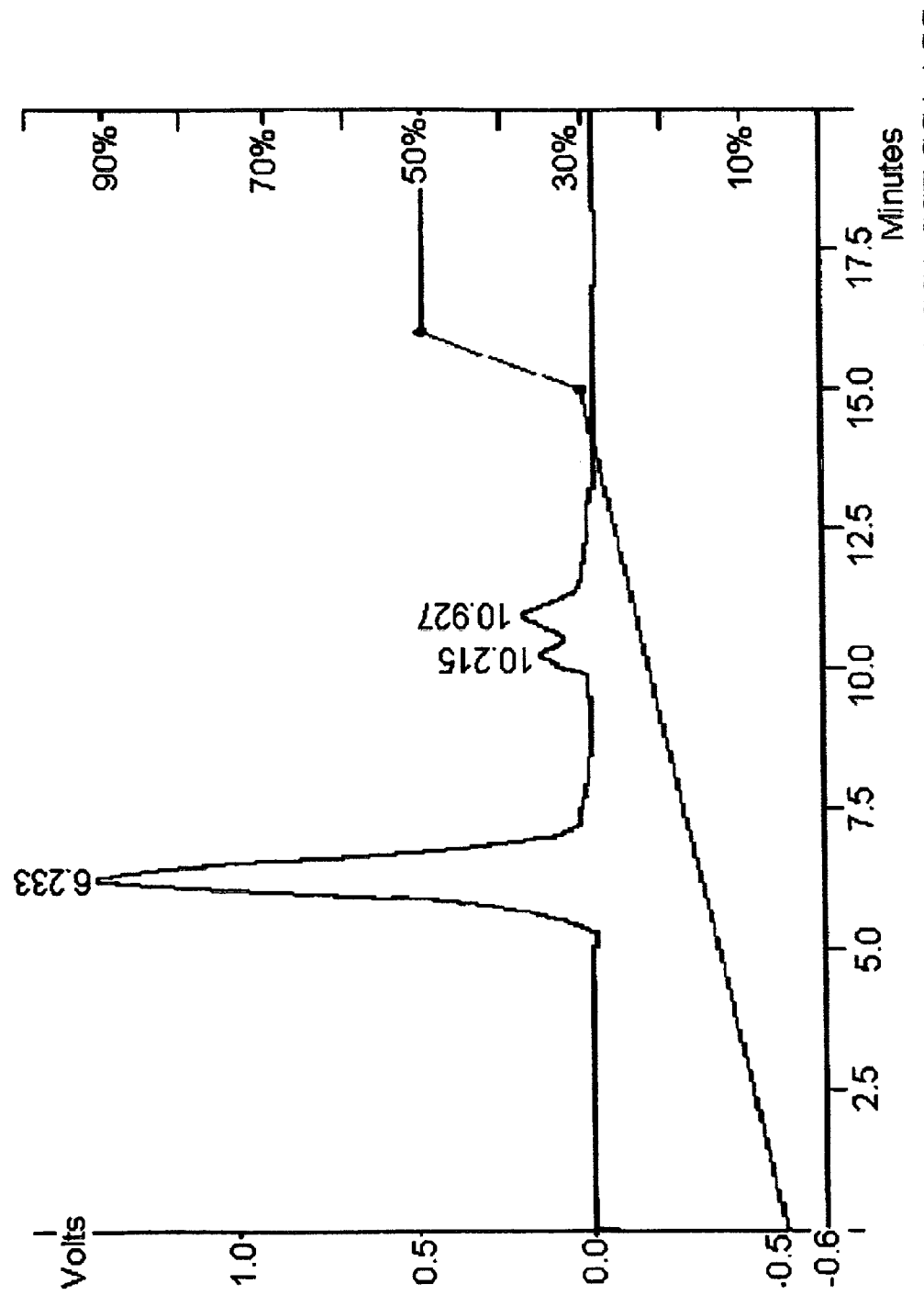
Figure 7A: HPLC analysis of the oligonucleotide sequence I.D.#9. dFC GGA CGT GGA ACG 120302sc1117a: dFC GGA CGT GGA ACG (SEQ ID NO:9)

| Peak No | Ret Time(min) | Peak Name Result (%) | Peak Area (counts) | Peak Height (counts) |
|---|---|---|---|---|
| 1 | 6.233 | 85.34 | 62403828 | 1397338 |
| 2 | 10.215 | 4.82 | 3527638 | 139172 |
| 3 | 10.927 | 9.84 | 7193832 | 190294 |
| Totals | | 100.00 | 73125296 | 1726804 |

Figure7B: HPLC analysis of the oligonucleotide sequence I.D.#9. dFC GGA CGT GGA ACG

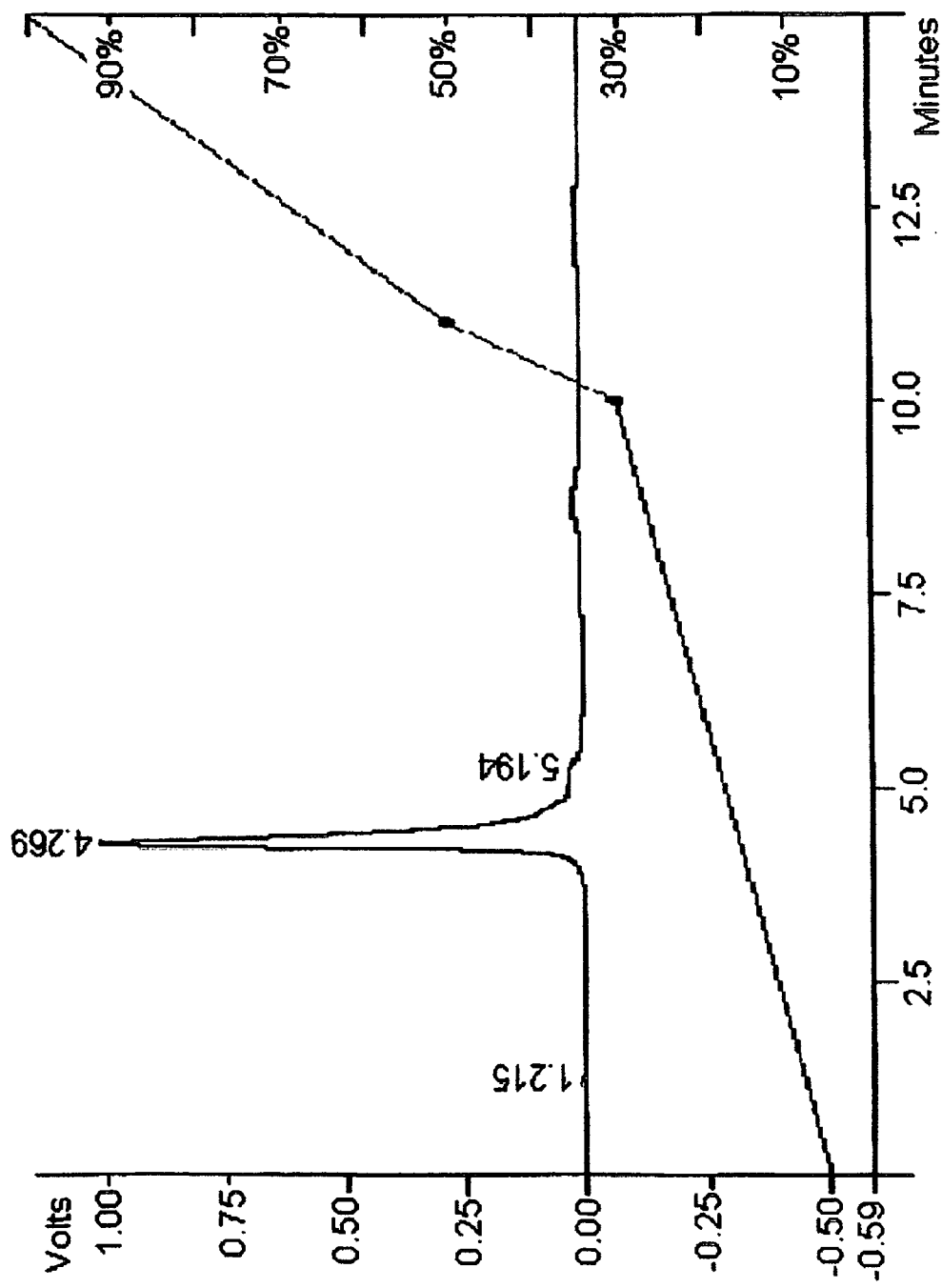
Figure 8A: HPLC analysis of the oligonucleotide sequence I.D. #10. dFC GGA GCT GGA ACG 120402sc1119a: dFC GGA GCT GGA ACG (SEQ ID NO: 10)

| Peak No | Ret Time(min) | Peak Name Result (%) | Peak Area (counts) | Peak Height (counts) |
|---|---|---|---|---|
| 1 | 1.215 | 0.27 | 36939 | 5231 |
| 2 | 4.269 | 99.29 | 13551755 | 991073 |
| 3 | 5.194 | 0.44 | 59924 | 7225 |
| Totals | | 100.00 | 13648618 | 1003529 |

Figure 8B: HPLC analysis of the oligonucleotide sequence I.D. #10. dFC GGA GCT GGA ACG

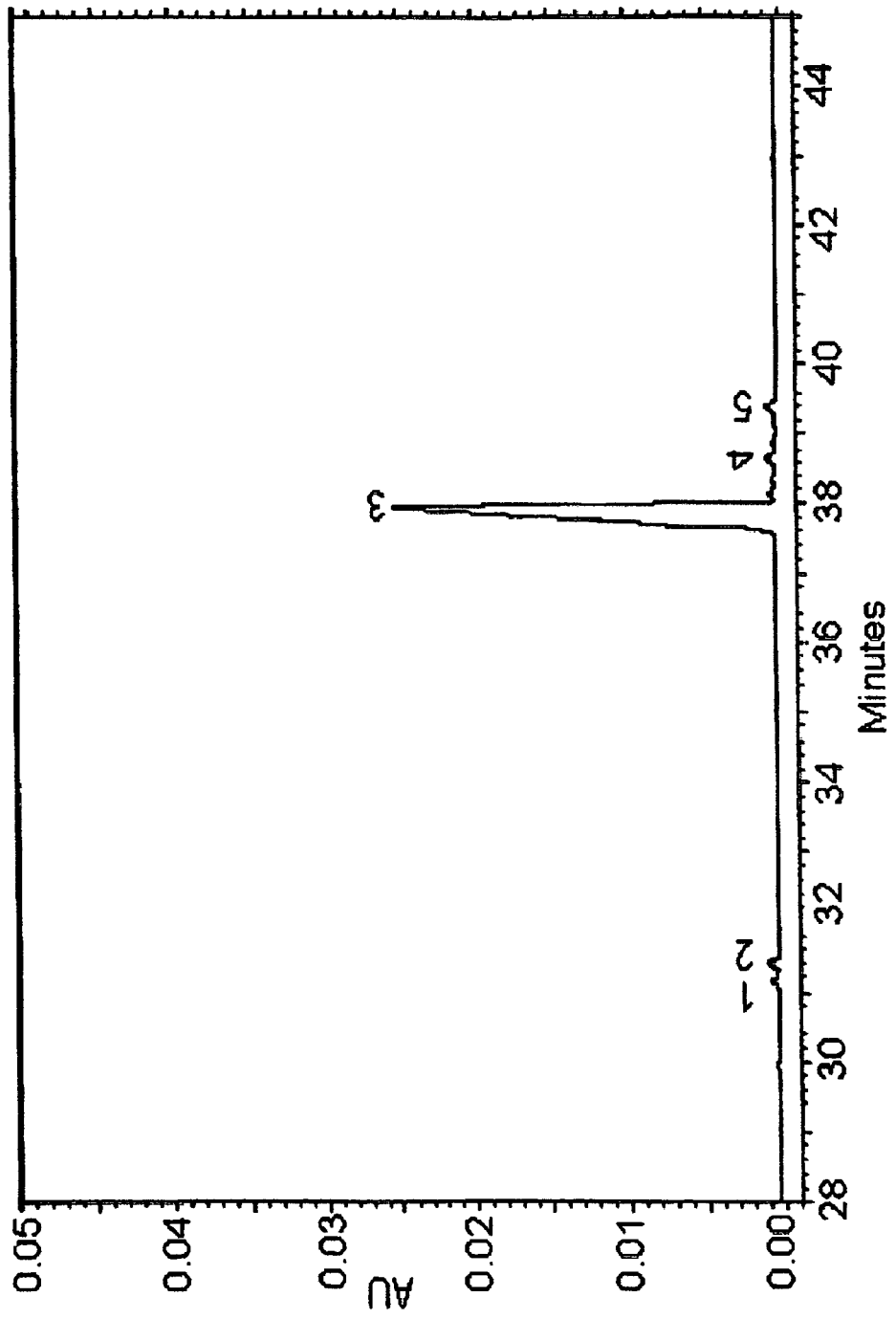
Figure 9A: Capillary Gel Electrophoresis of the oligonucleotide sequence I.D. #7. dFC GG ACG 120202sc1111a: dFC GG ACG  (SEQ ID NO:7)
UV – 254nm
Results

| Pk # | Migration Time | Area Percent |
|---|---|---|
| 1 | 31.133 | 0.699 |
| 2 | 31.408 | 0.964 |
| 3 | 37.904 | 96.167 |
| 4 | 38.646 | 0.826 |
| 5 | 39.392 | 1.343 |
| Totals | | 100.000 |

Sample concentration = 5.0 OD/ml: Injection time = 4.0 sec: Injection voltage = 10 kV:
Separation voltage = 16 kV

Figure 9B: Capillary Gel Electrophoresis of the oligonucleotide sequence I.D. #7. dFC GG ACG

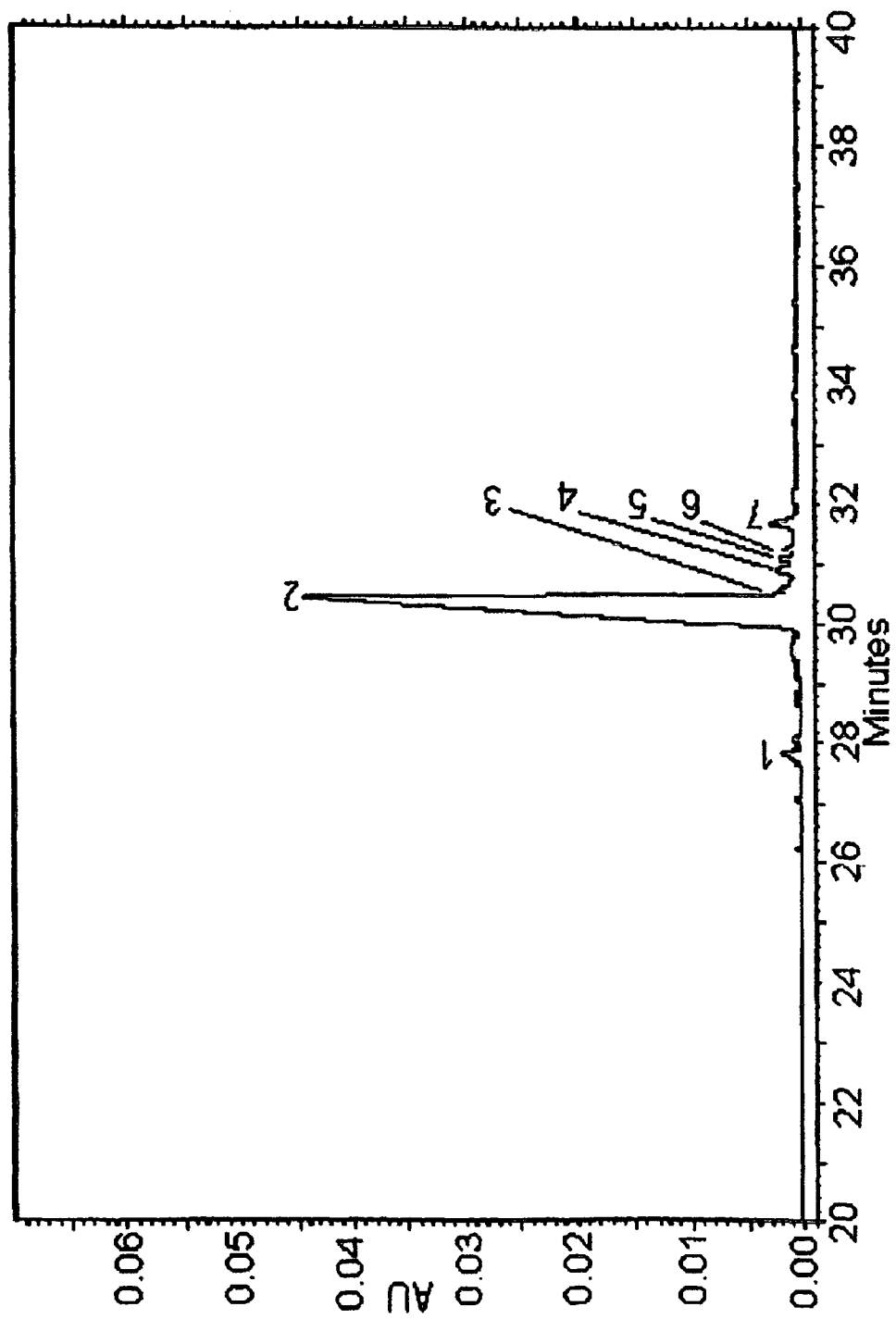
Figure 10A: Capillary Gel Electrophoresis of the oligonucleotide sequence I.D. #8. dFC GT GGA ACG 120202sc1113a: dFC GT GGA ACG (SEQ ID NO:8)

UV - 254nm
Results

| Pk # | Migration Time | Area Percent |
|------|----------------|--------------|
| 1 | 27.813 | 1.206 |
| 2 | 30.400 | 94.869 |
| 3 | 30.538 | 0.369 |
| 4 | 30.892 | 0.748 |
| 5 | 31.071 | 0.424 |
| 6 | 31.258 | 0.530 |
| 7 | 31.667 | 1.854 |
| Totals | | 100.000 |

Sample concentration = 5.0 OD/ml:  Injection time = 4.0 sec:  Injection voltage = 10 kV:
Separation voltage = 16 Kv Figure 10B: Capillary Gel Electrophoresis of the oligonucleotide sequence I.D. #8. dFC GT GGA ACG

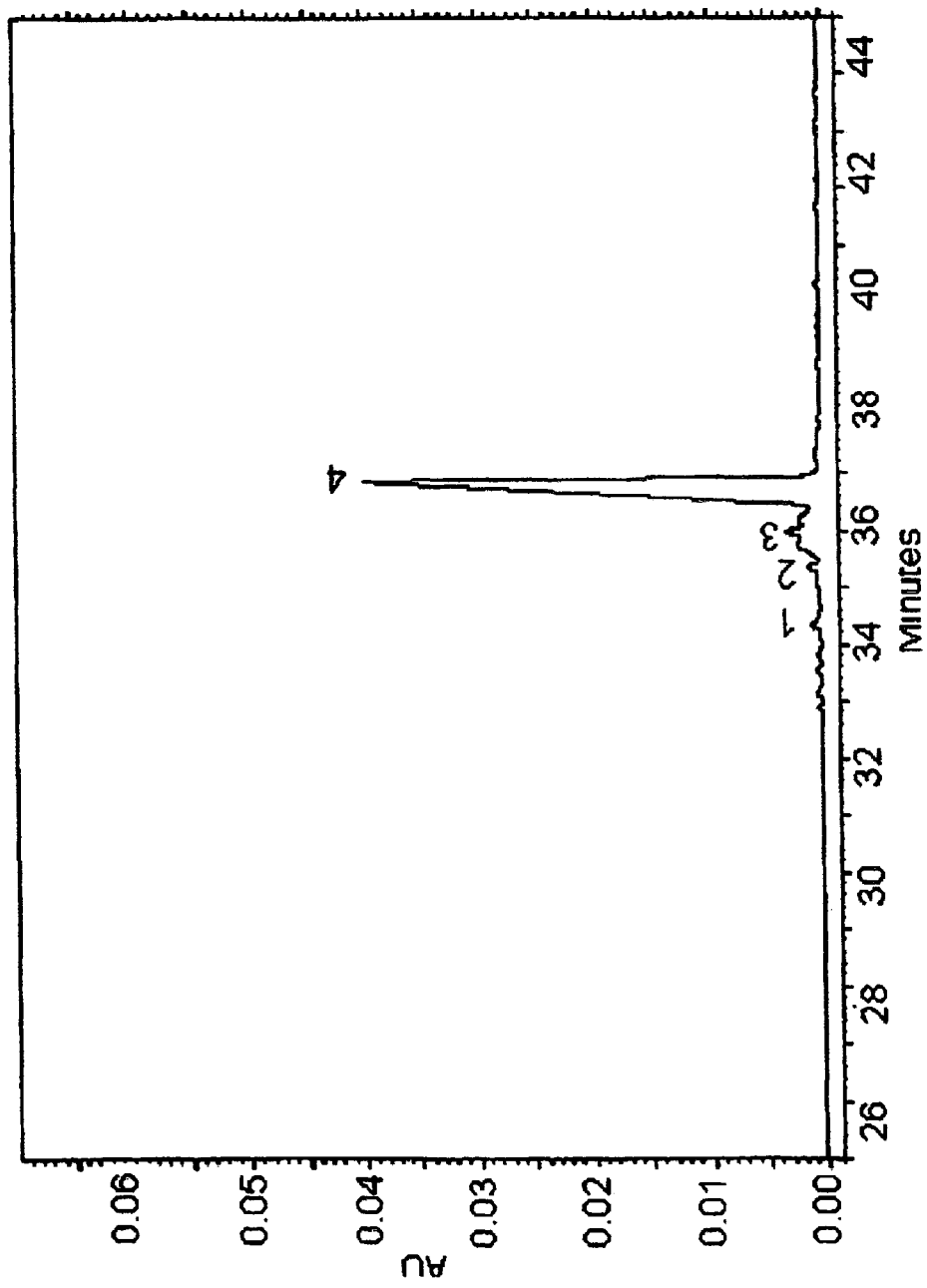
Figure 11A: Capillary Gel Electrophoresis of the oligonucleotide sequence I.D. #9. dFC GGA CGT GGA ACG 120302sc1117a: dFC GGA CGT GGA ACG (SEQ ID NO:9)

UV - 254nm
Results

| Pk # | Migration Time | Area Percent |
|---|---|---|
| 1 | 34.308 | 0.996 |
| 2 | 35.342 | 0.858 |
| 3 | 35.958 | 5.222 |
| 4 | 36.825 | 92.923 |
| Totals | | 100.000 |

Sample concentration = 5.0 OD/ml : Injection time = 4.0 sec: Injection voltage = 10 kV:
Separation voltage = 16 kV

Figure 11B: Capillary Gel Electrophoresis of the oligonucleotide sequence I.D. #9. dFC GGA CGT GGA ACG

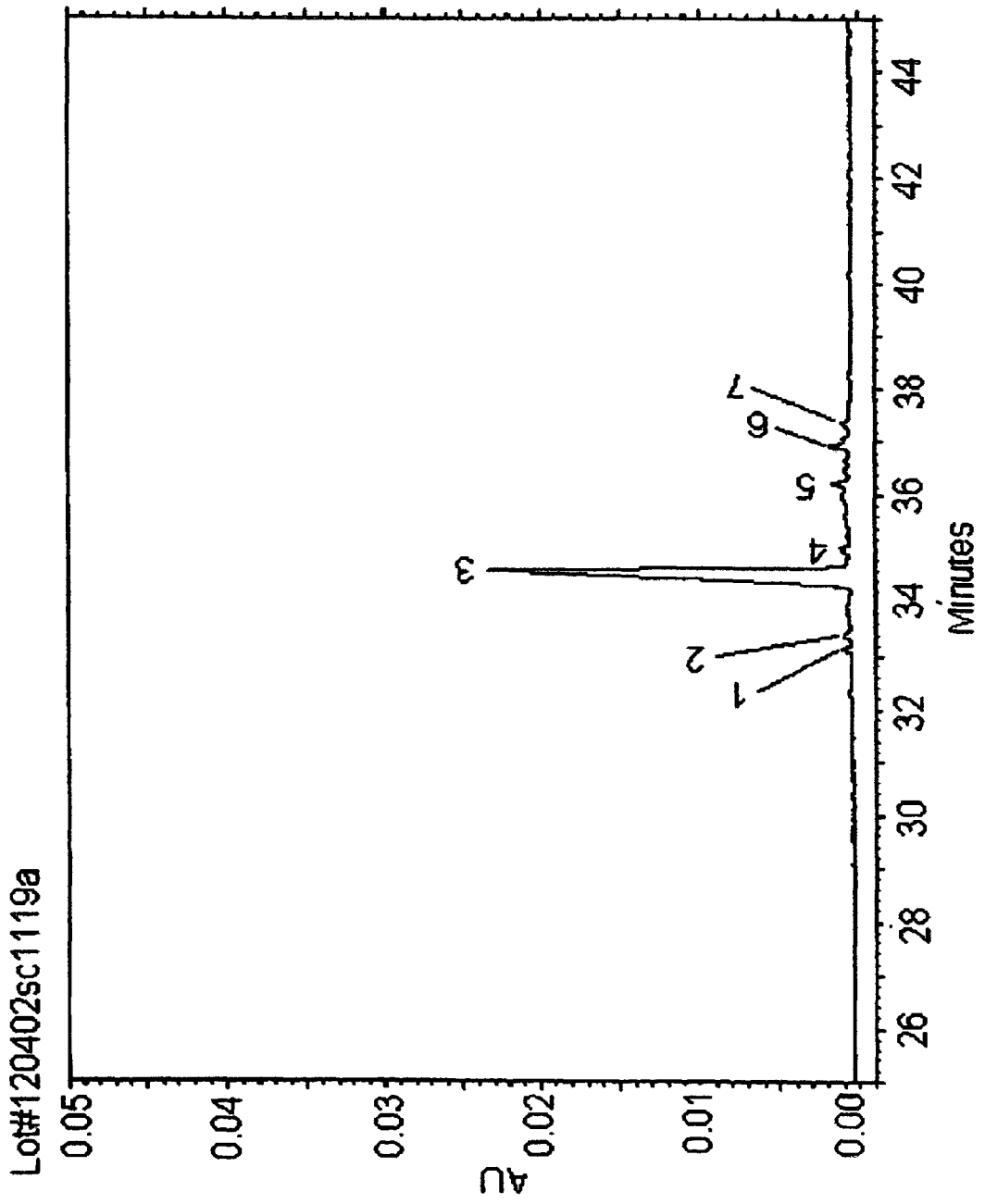
Figure 12A: Capillary Gel Electrophoresis of the oligonucleotide sequence I.D.#10. dFC GGA GCT GGA ACG 120402sc1119a: dFC GGA GCT GGA ACG (SEQ ID NO: 10)

UV - 254nm
Results

| Pk # | Migration Time | Area Percent |
|---|---|---|
| 1 | 33.142 | 1.103 |
| 2 | 33.400 | 1.195 |
| 3 | 35.029 | 1.717 |
| 5 | 36.246 | 1.132 |
| 6 | 36.913 | 1.842 |
| 7 | 37.054 | 0.473 |
| Totals | | 100.000 |

Sample concentration = 5.0 OD/ml: Injection time = 4.0 sec: : Separation voltage = 16 kV Figure 12B: Capillary Gel Electrophoresis of the oligonucleotide sequence I.D.#10. dFC GGA GCT GGA ACG

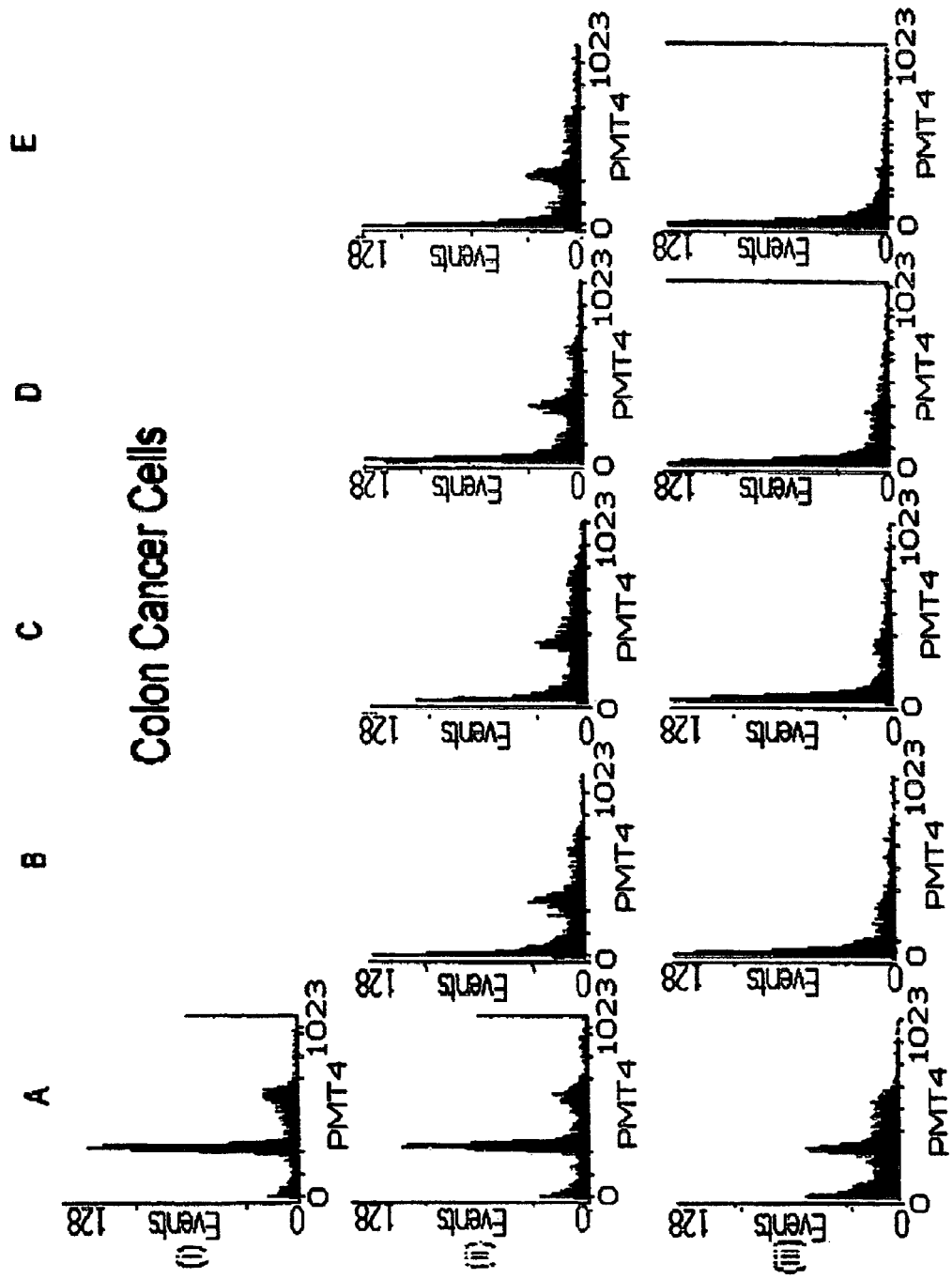
Figure 13: Flow Cytometric DNA cell cycle profiles: Effect of GEMCITABINE-ODN's on colon cancerous cells HT29

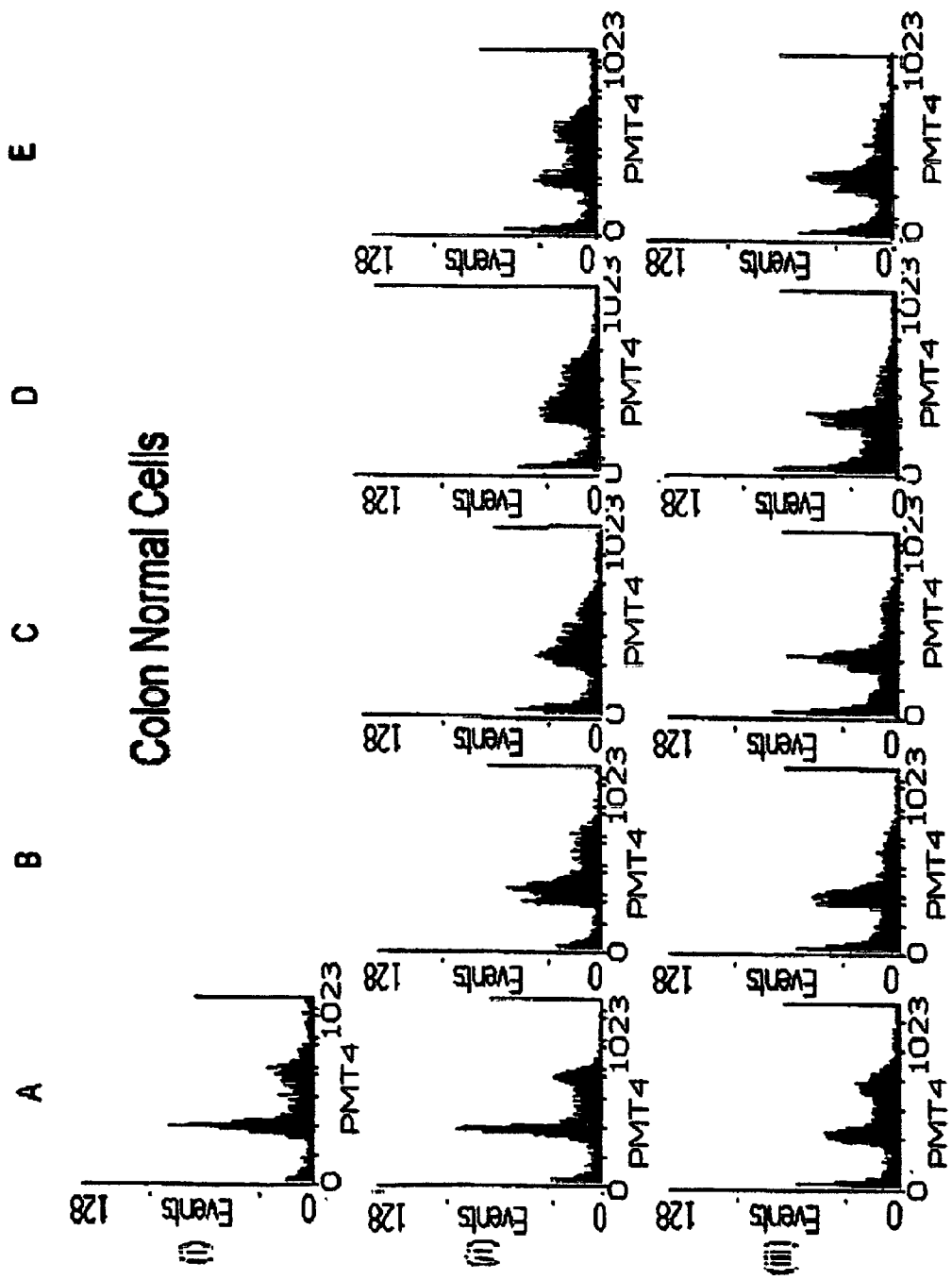
Figure 14: Flow Cytometric DNA cell cycle profiles: Effect of GEMCITABINE-ODN's on colon normal cells CCD-112CO

OLIGONUCLEOTIDES AND RELATED COMPOUNDS

CROSS-REFERENCE TO RELATED APPLICATIONS

This application claims priority to provisional application Ser. No. 60/525,691, filed on Nov. 28, 2003, entitled "CpG Oligonucleotides as carriers of Drugs-Gemcitabine—CpG Oligonucleotides as Highly Promising Anticancer Agents", which is hereby incorporated by reference.

FIELD OF THE INVENTION

The present application relates generally to oligonucleotides and more specifically to oligonucleotides which have a sequence including at least two CpG dinucleotides and a prodrug of an antimetabolite. The prodrug can be part of a CpG dinucleotide or may be attached elsewhere on the oligonucleotide. Intermediaries are further disclosed.

BACKGROUND OF THE INVENTION

According to statistics published on the homepage of the American Cancer Society, cancer accounts for nearly one-quarter of deaths in the United States, exceeded only by heart disease. In 2000, there were 553,091 cancer deaths in the US. A number of nucleoside analogues are currently used to treat different types of cancers, HIV and other disorders. Some of these are shown in Table 1, below.

TABLE 1

Anti-Cancer Agents

| Common or trade name | CAS number | Formula |
|---|---|---|
| Lamivudin | 134678-17-4 | 2'-deoxy-3'-thiacytidine |
| Zidovudine | 30516-87-1 | 3'-azido-3'-deoxythymidine |
| Zalcitabine | 7481-89-2 | 2',3'-dideoxycytidine |
| Stavudine | 3056-17-5 | 2',3'-didehydro-3'-deoxythymidine |
| didanosine | 69655-05-6 | 2',3'-dideoxyinosine, |
| Abacavir | 136470-78-5 | 2-Cyclopentene-1-methanol, 4-[2-amino-6-(cyclopropylamino)-9H-purin-9-yl]-, (1S,4R)-(9CI) |
| floxuridine | 50-91-9 | 5-fluoro-2'-deoxy uridine |
| fludarabine | 21679-14-11 | 2-fluoro-9-b-D-arabinofuranosyladenine |
| Cytarabine | 147-94-4 | 1-B-D-arabinofuranosylcytosine |
| azacitidine | 320-67-2 | 5-azacytidine |
| Decitabine | 2353-33-5 | 5-aza-2'-deoxycytidine |
| Thioinosine | 22140-20-1 | 6-mercaptopurineriboside |
| | 85-31-4 | 6-thioguanosine |
| cladribine | 4291-63-8 | 2-chlorodeoxyadenosine |
| pentostatin | 53910-25-1 | 2' deoxycoformycin |
| Gemcitabine | 95058-81-4 | 2'-deoxy, 2',2'-difluorocytosine |

It has been shown recently that the human genome has highly conserved metameric GCn*GC motif clusters located across genes and promoter regions. Such GCn*GC sites are vulnerable genomic sites that are preferentially destroyed in both apoptotic and necrotic cell death commitment, with specific megabase DNA fragmentations revealed in pulsed-field gel electrophoretic data analysis. (Yee-Jiun Kok, Myint Swe, and Kwok-Hung Sit, Biochemical and Biophysical Communications, 294: 934-939, 2002).

Normal cells are euploid and do not have drug/multidrug resistance. Cancerous cells, on the other hand, have a continuously evolving aneuploid phenotype resulting from high genetic instability and vulnerability, which is associated with high mutational rates, and drug and multidrug resistance (PNAS 98: 11283-11288, 2001; PNAS 97: 14295-14300, 2000; Cancer Genet. Cytogenet. 119: 83-93, 2000; Nature Biotechnology 19: 22-23, 2000).

Untargeted genomic destruction by treatment with many anticancer drugs does cause cell death. Gemcitabine, for example, is most likely incorporated into DNA as a competitive inhibitor of deoxycytidine by the de novo DNA synthesis pathway. Gemcitabine is a prodrug, which most likely gets phosphorylated in the cell to be active. It has been shown to be a better permeant than cytrabine (arabinosylcytosine), another anticancer drug (Biochemical Pharmacology 46(4): 762-766, 1993). The nucleoside is a favorable substrate for deoxycytidine kinase, and thus accumulates in cells in greater amounts. Further, the formation of Gemcitabine triphosphate and its negative feedback regulation of deoxycytidine deaminase, results in favorable incorporation of Gemcitabine via its triphosphate, into DNA. The incorporation of Gemcitabine into DNA results in cell death. Gemcitabine has a vastly improved therapeutic index as compared to many anticancer drugs. However this cell death remains non-specific to cancerous cells in that death is induced equally in both cancerous and normal cells. Thus, although Gemcitabine (Gemzar) (like other anticancer drugs) is effective in causing cell death and is approved by the FDA for the treatment of a range of cancers, there is no differential killing between normal and cancer cells in non-targeted continuous treatment (See, e.g., Eli Lilly publication attached hereto as Appendix A).

There is therefore an urgent need for an approach in which selective targeting of potent anticancer drugs to cancer cells can be achieved.

It has been shown by recent studies (Biochem. Biophy. Res. Commun. 294: 934-939, 2002) that cell death, whether by necrosis or apoptosis, has orderly DNA fragmentation. Thus kilobase and 200 by DNA ladder fragmentations obtained by way of necrosis from freezing, demonstrated a marked pattern of DNA base sequence selection, similar to that in apoptosis. The genomic GC clusters with high density were preferentially GCn*GC (SEQ ID NO: 1) a motifs. They seem to align with metameric regularity in the genome of man to virus, and thus preserve a high degree of regularity in the chromatin conformation.

Necrosis from freezing manifested an orderly pattern of DNA fragmentations including the apoptosis signature of 200 by ladder, in three different cell populations despite pancan-pase suppression by zVAD-fmk. Immediately on thawing, all three populations had 100% dead cell indices and 2.2, 1.6, and 1.1 megabase fragmentations, which marked the point of death. Kilobase and 200 by DNA ladder fragmentations manifested later together with overt necrotic morphologies. CpG oligodeoxynucleotides (ODNs) complementary to highly conserved GCnGC (SEQ ID NO: 2) motifs inhibited the megabase fragmentations and retarded their electrophoretic mobility (gel shift), indicating ODN-DNA binding, which is known to confer site-specific resistance to cleavage. Cleavage specificity was confirmed using EDTA-CpG ODN conjugates to direct free-radical-producing transitional element, vanadyl(4), to the binding sites to reproduce the megabase fragmentations in normal cells. Specific orderly fragmentation in necrosis suggested a necrosis-apoptosis convergence after death has been committed (Biochem. Biophy. Res. Commun. 294: 934-939, 2002).

Thus, in a recent study, it was shown that the complementary CGn*CG (SEQ ID NO: 3) oligodeoxynucleotide (ODN) sequences in parallel orientation were able to inhibit megabase DNA fragmentation, indicating ODN-DNA binding, and thereby conferring site-specific resistance to cleavage (Biochem. Biophy. Res. Commun. 294: 934-939, 2002). A series of ODN, with GCn*GC (SEQ ID NO: 1) motifs, where n=2, 5, 9, were synthesized in this study. The test examples synthesized were 5'-GCnnGC-3' (SEQ ID NO: 4), 5'-GCnnnnnGC-3' (SEQ ID NO: 5), 5'-GCnnn nnn nnn GC-3' (SEQ ID NO: 6). These oligonucleotides, which are complementary to the highly conserved GCn*GC motifs, after conjugation inhibited the megabase fragmentations, thereby indicating ODN-DNA binding.

Few other CpG motifs are widespread in nature. It has been stated that certain CpG oligonucleotides stimulate strong, balanced immunity by boosting antibody based cellular responses to antigens presented by infectious pathogens or cancerous cells. Based on this approach a CpG oligonucleotide developed is currently on clinical trial, phase I/phase II, as a monotherapy or multidrug therapy for non-Hodgkins' lymphoma, basal cell carcinoma and melanoma (Eugene Uhlmann, in the Oligonucleotide and Peptide Conferences, May 6-8 Tides 2002, Las Vegas, Nev.).

Bacterial DNA has been shown to contain CpG DNA. CpG DNA has been shown to stimulate B-cell proliferation and activate macrophages, monocytes and dendritic cells. The activation of immune cells by CpG DNA results in the secretion of a number of cytokines, including IL-6, IL-12, TNF-a and TNF-r (Wagner, H. (2000) Immunology of Bacterial CpG-DNA, Springer-Verlag, Heidelberg, Germany; Raz, E. (2000) Immunostimulatory DNA sequences. Springer-Verlag, Heidelberg, Germany). Thus, divergent therapeutic and immunologic effects of oligonucleotides with CpG motifs have been reported (Ballas, Z. K., Krieg, A. M., Warren, T., Rasmussen, W., Davis, H. L., Waldschmidt, M. and Wagner, G. J., J. Immunol. 167, 4878-4886, 2001). CpG DNA has been similarly shown to overcome hyporesponsiveness to Hepatitis B vaccine in orangutans. (Davis, H. L., Suparto, I. I., Weeratna, R. R., Jumintarto, Iskandriati, D. D., Chamzah, S. S., Ma'ruf, A. A., Nente, C. C., Pawitri, D. D., Krieg, A. M., Vaccines, 18: 1920-1924, 2000). CpG oligonucleotides have been shown to trigger protective and curative ThI responses in lethal murine leishmaniasis (Zimmermann, S., Egeter, O., Hausmann, S., Lipford, G. B., Rocken, M., Wagner, H., Heeg, K. J. Immunol., 160: 3627-3630, 1998). More recently synthetic phosphorothiate oligonucleotides containing CpG dinucleotides were shown to possess immunostimulatory activity (Dong Yu, Ekamber R. Kandimalla, Qiuyan Zhao, Yanping Cong and Sudhir Agarwal, Nucleic Acids Res., 30: 1613-1619, 2002). Further, these authors reported novel 3',3'-linked CpG oligodeoxynucleotides as potent immunostimulatory agents with key design and two or more identical CpG DNA segments (Dong Yu, Ekamber R. Kandimalla, Lakshmi Bhagat, Jin Yan Tang, Yanping Cong, Jimy Tang and Sudhir Agarwal, Nucleic Acids Res., 30: 4460-4469, 2002). In a recent study improved oligodeoxynucleotides (ODN) have been synthesized having a CpR motif, which have potent immunostimulatory properties, and cause increased induction of interleukin (IL)-12 and lesser secretion of IL-6 (Ekamber R. Kandimalla, Lakshmi Bhagat, Daqing Wang, Dong Yu, Fu-Gang Zhu, Jimmy Tang, Hui Wang, Ping Huang, Ruiwen, and Sudhir Agarwal, Nucl. Acids Res., 31: 2393-2400, 2003).

SUMMARY

In one embodiment, the invention provides an oligonucleotide for preferentially killing cancerous cells over non-cancerous cells, comprising at least two CpG moieties and a prodrug for an antimetabolite covalently linked to the oligonucleotide. In one embodiment, the antimetabolite is selected from the group consisting of 2'-deoxy-3'-thiacytidine, 3'-azido-3'-deoxythymidine, 2',3'-dideoxycytidine, 2',3'-didehydro-3'-deoxythymidine, 2',3'-dideoxyinosine, 5-fluoro-2'-deoxy uridine, 2-fluoro-9-b-D-arabinofuranosyladenine, 1-B-D-arabinofuranosylcytosine, 5-azacytidine, 5-aza-2'-deoxycytidine, 6-mercaptopurineriboside, 2-chlorodeoxyadenosine, and pentostatin. In another embodiment, it is selected from 2'-deoxy-3'-thiacytidine, 3'-azido-3'-deoxythymidine, 2',3'-didehydro-3'-deoxythymidine, 2',3'-dideoxyinosine, 5-fluoro-2'-deoxyuridine, 2-fluoro-9-b-D-arabinofuranosyladenine, 1-B-D-arabinofuranosylcytosine 5-azacytidine, 5-aza-2'-deoxycytidine, 6-mercaptopurineriboside, 6-thioguanosine, 2-chlorodeoxyadenosine, pentostatin, and 2'-deoxy, 2',2'-difluorocytosine. Preferably, the prodrug is one for the antimetabolite 2'-deoxy, 2',2'-difluorocytidine. In some embodiments, the two of the at least two CpG moieties are separated by a number of nucleotides selected from the numbers 2, 5, and 9. In one embodiment, the prodrug is 5' to the at least two CpG moieties. In another embodiment, the prodrug is 3' to the at least two CpG moieties. In yet another embodiment, the prodrug is 3' to at least one CpG moiety and 5' to at least a second CpG moiety. The prodrug can be linked to the oligonucleotide by a 3'-3' linkage, a 5'-5' linkage, a 3'-5' linkage, or a 5'-3' linkage. In one embodiment, the prodrug is at a position that is selected from 10 nucleotides upstream from one of the at least two CpG moieties, 9 nucleotides upstream from the CpG moiety, 8 nucleotides upstream from the CpG moiety, 7 nucleotides upstream from the CpG moiety, 6 nucleotides upstream from the CpG moiety, 5 nucleotides upstream from the CpG moiety, 4 nucleotides upstream from the CpG moiety, 3 nucleotides upstream from the CpG moiety, 2 nucleotides upstream from the CpG moiety, 1 nucleotides upstream from the CpG moiety, 10 nucleotides downstream from a CpG moiety, 9 nucleotides downstream from the CpG moiety, 8 nucleotides downstream from the CpG moiety, 7 nucleotides downstream from the CpG moiety, 6 nucleotides downstream from the CpG moiety, 5 nucleotides downstream from the CpG moiety, 4 nucleotides downstream from the CpG moiety, 3 nucleotides downstream from the CpG moiety, 2 nucleotides downstream from the CpG moiety, and 1 nucleotides downstream from the CpG moiety. In another embodiment, the prodrug is covalently linked to the oligonucleotide by a linker having the formula:

Linker;

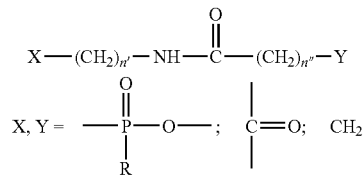

In some embodiments, the oligonucleotides of the invention include at least one nucleotide having a ribose sugar moiety. In other embodiments, the oligonucleotides of the invention include at least one nucleotide having a 2'-deoxyribose sugar moiety.

In yet other embodiments, the oligonucleotides of the invention include at least one 2'-halogen nucleotide. In yet other embodiments, the oligonucleotides of the invention include at least one 2'-N-alkyl nucleotide wherein the alkyl has between about 1 and about 6 carbon atoms. In yet other embodiments, the oligonucleotides of the invention include at least one 2'-O-alkyl nucleotide, one 2'-N-Alkyl nucleotide, or one 2'-O-halogen nucleotide, wherein the alkyl has between about 1 and about 6 carbon atoms. In these embodiments, the alkyl is preferably methyl. The oligonucleotides of the invention include a plurality of nucleotides connected by covalent internucleoside linkages, wherein each of the linkages is selected from the group consisting of a phosphodiester linkage, a C1-C6 alkoxy phosphotriester linkage, a phosphorothioate linkage and a phosphoramidate linkage.

The invention further provides a pharmaceutical composition that includes a therapeutically effective amount of one or more of the oligonucleotides of the invention. Preferably, the pharmaceutically acceptable carrier is lipofectin.

In yet another embodiment, the invention provides an oligonucleotide for preferentially killing cancerous cells over non-cancerous cells, having a motif represented by the formula: 5'PGXCG3' wherein P is a prodrug for an antimetabolite and X represents between 0 and 50 nucleotides. Preferably, X is 2, 5, or 9. Further, the antimetabolite most preferred is 2'-deoxy, 2'-,2'-difluorocytidine. In one embodiment, the antimetabolite is selected from the group consisting of 2'-deoxy-3'-thiacytidine, 3'-azido-3'-deoxythymidine, 2',3'-dideoxycytidine, 2',3'-didehydro-3'-deoxythymidine, 2',3'-dideoxyinosine, 5-fluoro-2'-deoxy uridine, 2-fluoro-9-b-D-arabinofuranosyladenine, 1-B-D-arabinofuranosylcytosine, 5-azacytidine, 5-aza-2'-deoxycytidine, 6-mercaptopurineriboside, 2-chlorodeoxyadenosine, or pentostatin. In another embodiment, the antimetabolite is selected from 2'-deoxy-3'-thiacytidine, 3'-azido-3'-deoxythymidine, 2',3'-didehydro-3'-deoxythymidine 2',3'-dideoxyinosine, 5-fluoro-2'-deoxyuridine, 2-fluoro-9-b-D-arabinofuranosyladenine, 1-B-D-arabinofuranosylcytosine 5-azacytidine, 5-aza-2'-deoxycytidine, 6-mercaptopurineriboside, 6-thioguanosine, 2-chlorodeoxyadenosine, pentostatin, and 2'-deoxy, 2',2'-difluorocytosine. In some embodiments, the prodrug is covalently linked to one of the nucleotides of the oligonucleotides of the invention by a 3'-3' linkage, a 5'-5' linkage, a 3'-5' linkage, or a 5'-3' linkage. In one embodiment, the oligonucleotide of the invention has at least one nucleotide having a ribose sugar moiety. In another embodiment, the oligonucleotide of the invention has at least one nucleotide having a 2'-deoxyribose sugar moiety. In yet another embodiment, the oligonucleotide has at least one 2'-O-Alkyl nucleotide, 2'-N-Alkyl nucleotide, or 2'-O-halogen nucleotide, wherein the alkyl has between about 1 and about 6 carbon atoms. Nucleotides of the oligonucleotides are connected by covalent internucleoside linkages. Examples of covalent internucleoside linkages include phosphodiester linkages, C1-C6 alkoxy phosphotriester linkages, phosphorothioate linkages and phosphoramidate linkages. In some embodiments, the prodrug is attached to at least one of the multiple nucleotides by a linker of the following formula:

Linker;

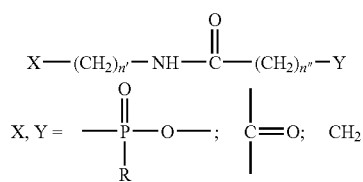

The invention further provides a pharmaceutical composition that includes a therapeutically effective amount of any of the oligonucleotides disclosed herein. In some embodiments, the pharmaceutically acceptable carrier is lipofectin.

The invention further provides a compound having purity in excess of 98% by HPLC, and having the following formula:

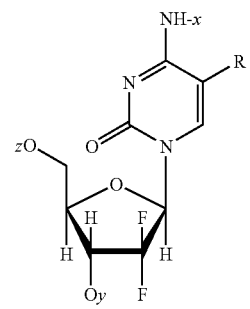

wherein R is selected from the group consisting of H, a C1-C6 alkyl, a halogen, a C2-C6 alkenyl, and a C2-C6 alkynyl;

x is an amine-protecting group that is stable in oligonucleotide synthesis conditions; and y, and z are each selected from H, a hydroxyl-protecting group that is stable in oligonucleotide synthesis conditions and a group that can be attached to a solid support. In some embodiments, the compound group that is attachable to a solid support has the formula O—C(=O)-M-C(=O)—NH-Spacer, where M is selected from the group consisting of succinyl, oxalyl, and hydroquinolynyl, and wherein the Spacer is a C1-C6 alkyl, ethyloxyglycol, or a combination of alkyl and ethyleneglycoxy, and the Spacer is attached to the solid support.

The invention further provides a compound having the formula:

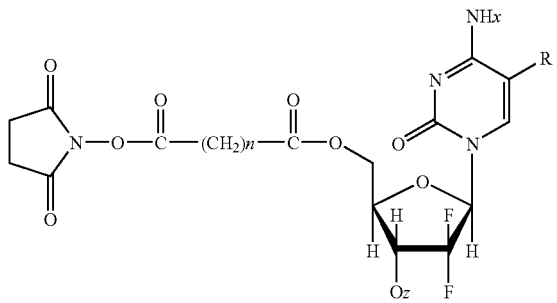

wherein R is selected from the group consisting of H, a C1-C6 alkyl, a halogen, a C2-C6 alkenyl, and a C2-C6 alkynyl;

x is an amine-protecting group that is stable in oligonucleotide synthesis conditions;

z is a hydroxyl-protecting group that is stable in oligonucleotide synthesis conditions; and n is 2-20.

Additionally, the following compound is provided, having the formula:

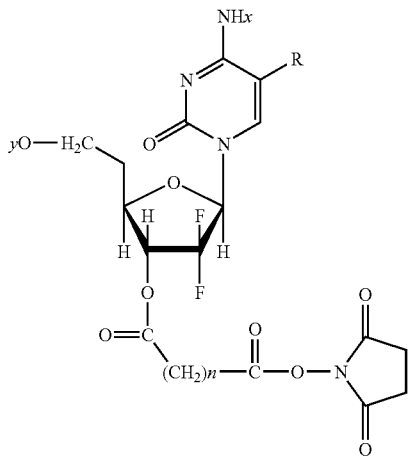

wherein R is selected from the group consisting of H, a C1-C6 alkyl, a halogen, a C2-C6 alkenyl, and a C2-C6 alkynyl;

x is an amine-protecting group that is stable in oligonucleotide synthesis conditions;

z is a hydroxyl-protecting group that is stable in oligonucleotide synthesis conditions; and n is 2-20.

The invention additionally provides a compound having a purity in excess of 97% by HPLC, as shown by the formula:

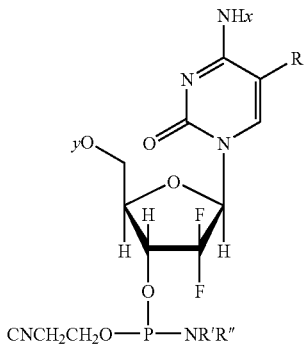

wherein y is a hydroxyl-protecting group that is stable in oligonucleotide synthesis conditions;

x is an amine-protecting group that is stable in oligonucleotide synthesis conditions;

R is selected from the group consisting of H, a C1-C6 alkyl, a halogen, a C2-C6 alkenyl, and a C2-C6 alkynyl; and R' and R" are independently selected and are either a C1-C6 alkyl or a C2-C6 cycloalkyl.

Additionally, the invention provides a compound having purity in excess of 97% by HPLC, and having the formula:

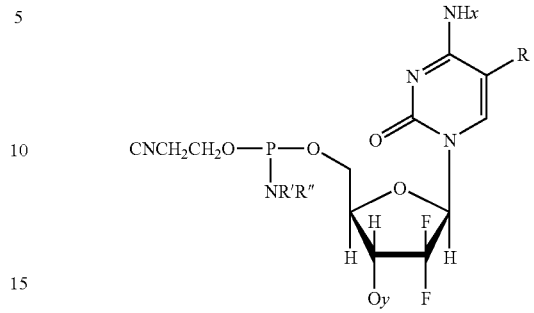

wherein y is a hydroxyl-protecting group that is stable in oligonucleotide synthesis conditions;

x is an amine-protecting group that is stable in oligonucleotide synthesis conditions;

R is selected from the group consisting of H, a C1-C6 alkyl, a halogen, a C2-C6 alkenyl, and a C2-C6 alkynyl; and R' and R" are independently selected from the group of either C1-C6 alkyls or C2-C6 cycloalkyls.

The studies of Dr. Kwok-Hung Sit and colleagues (Yee-Jiun Kok, Myint Swe, and Kwok-Hung Sit, Biochemical and Biophysical Communications, 294 934-939, 2002), suggest a relationship between the cell death and immunostimulatory activity. With the effective ODN-CpG binding, there is strong inhibition of CpG DNA fragmentation, resulting in site specific resistance to cleavage, and thereby prevent necrosis and apoptosis. CpG oligonucleotides referred in the preceding discussions, however, independently seem to enhance the immunostimulatory activity. On the other hand inhibition of megabase fragmentation of the highly conserved GCn*GC (SEQ ID NO; 1) motifs by complementary ODN's will help to protect complementary CpG DNA from degradation. Our approach of ODN design and incorporation of potent anticancer drug is a novel approach and presents enormous future potential in molecular medicine. The incorporated anticancer drug can be cleaved by one of the several endolytic cleavage mechanisms. This should result in hydrolysis of a phosphodiester bond, esterase hydrolysis of the ester linkages outlined in the details of claims or amidate hydrolysis will liberate the anticancer drug. While the CpG ODN will act as complementary DNA-ODN conjugate for the stability from degradation, it also seems that with proper design selection of the CpGn*CpG (SEQ ID NO: 3) ODN, immunostimulatory properties of the ODN could be available within the cell.

The hydrolysis of Gemcitabine (or another prodrug) which is attached via an ester linkage to a CpG oligo, is envisaged to be easily hydrolyzed by intracellular esterases (Ghosh, M and Mitra, A. K., Pharm. Res., 8, 771-775, 1009).

BRIEF DESCRIPTION OF THE DRAWINGS

FIG. 1 shows UV analysis graph between 220-320 nm of the sequence I.D.#7, sequence dFC GG ACG, lot #120202sc1111a, and the chart below the graph shows the absorbance at 250 nm, 260 nm and 280 nm, along with the ratio of absorption between 250/260 and 260/280. The UV absorption maxima is noted at 256 nm.

FIG. 2 shows UV analysis graph between 220-320 nm of the sequence I.D.#8, sequence dFC GTG GAA CG, lot

120202sc1113a, and the chart below the graph shows the absorbance at 250 nm, 260 nm and 280 nm, along with the ratio of absorption at 250/260 and 260/280. The UV absorption maxima is noted at 256 nm.

FIG. 3 shows UV analysis graph between 220-320 nm of the sequence I.D.#9, sequence dFC GGA CGT GGA ACG, lot #120202sc1117a, and the chart below the graph shows the absorbance at 250 nm, 260 nm and 280 nm, along with the ratio of absorption at 250/260 and 260/280. The UV absorption maxima is noted at 256 nm.

FIG. 4 shows UV analysis graph between 220-320 nm of the sequence I.D.#10, sequence dFC GGA GCT GGA ACG, lot #120202sc1119a, and the chart below the graph shows the absorbance at 250 nm, 260 nm and 280 nm, along with the ratio of absorption at 250/260 and 260/280. The UV absorption maxima is noted at 257 nm.

FIG. 5A shows HPLC analysis tracing of the sequence I.D.#7, sequence dFC GG ACG, lot #120202sc1111a with the run time of 20 minutes. The gradient profile is drawn as horizontal line going across the tracing. The gradient used has been discussed in the material and methods section.

FIG. 5B shows the chart of HPLC analysis report of the sequence I.D.#7, sequence dFC GG ACG, lot #120202sc1111a, with the listings of the peaks observed, their retention time in minutes, peak area, peak height, group, separation code.

FIG. 6A shows HPLC analysis tracing of the sequence I.D.#8 sequence dFC GTG GAA CG, lot #120202sc1113a with the run time of 20 minutes. The gradient profile is drawn as horizontal line going across the tracing. The gradient used has been discussed in the material and methods section.

FIG. 6B shows the chart of HPLC analysis report of the sequence I.D.#8 sequence dFC GTG GAA CG, lot #120202sc1113a. The chart lists the peaks observed, their retention time in minutes, peak area, peak height, group, separation code.

FIG. 7A shows HPLC analysis tracing of the sequence I.D.#9 sequence, dFC GGA CGT GGA ACG, lot #120202sc1117a, with the run time of 20 minutes. The gradient profile is drawn as horizontal line going across the tracing. The gradient used has been discussed in the material and methods section.

FIG. 7B shows the chart of HPLC analysis report of the sequence I.D.#9 dFC GGA CGT GGA ACG, lot #120202sc1117a. The chart lists the peaks observed, their retention time in minutes, peak area, peak height, group, separation code.

FIG. 8A shows HPLC analysis tracing of the sequence I.D.#10 sequence, dFC GGA GCT GGA ACG, lot #120202sc1119a, with the run time of 20 minutes. The gradient profile is drawn as horizontal line going across the tracing. The gradient used has been discussed in the material and methods section.

FIG. 8B shows the chart of HPLC analysis report of the sequence I.D.#10 dFC GGA GCT GGA ACG, lot #120202sc1117a. The chart lists the peaks observed, their retention time in minutes, peak area, peak height, group, separation code.

FIG. 9A shows capillary gel electrophoresis (CE) analysis tracing at 254 nm of the sequence I.D.#7, sequence dFC GG ACG, lot #120202sc1111a. The run time of 45 minutes, sample concentration; 5.0 OD at 260 nm; injection time; 4.0 sec., injection voltage; 10 kV; separation voltage; 16 kV. The other details discussed in the material and methods section.

FIG. 9B shows the chart of CE analysis report of the sequence I.D.#7, sequence dFC GG ACG, lot #120202sc1111a, with the listings of the peaks observed, their migration time in minutes, area percent.

FIG. 10A shows capillary gel electrophoresis (CE), UV 254 nm, of the sequence I.D.#8 sequence dFC GTG GAA CG, lot #120202sc1113a with the run time of 45 minutes, sample concentration; 5.0 OD at 260 nm; injection time; 4.0 sec., injection voltage; 10 kV; separation voltage; 16 kV. The other details discussed in the material and methods section.

FIG. 10B shows the chart of CE analysis report of the sequence I.D.#8, sequence dFC GTG GAA CG, lot #120202sc1113a, with the listings of the peaks observed, their migration time in minutes, area percent.

FIG. 11A shows capillary gel electrophoresis (CE), UV 254 nm, of the sequence I.D.#9 sequence dFC GGA CGT GGA ACG, lot #120202sc1117a with the run time of 45 minutes, sample concentration; 5.0 OD at 260 nm; injection time; 4.0 sec., injection voltage; 10 kV; separation voltage; 16 kV. The other details discussed in the material and methods section.

FIG. 11B shows the chart of CE analysis report of the sequence I.D.#9, sequence dFC GGA CGT GGA ACG, lot #120202sc1117a, with the listings of the peaks observed, their migration time in minutes, area percent.

FIG. 12A shows capillary gel electrophoresis (CE), UV 254 nm, of the sequence I.D.#10 sequence dFC GGA GCT GGA ACG, lot #120202sc1119a with the run time of 45 minutes, sample concentration; 5.0 OD at 260 nm; injection time; 4.0 sec., injection voltage; 10 kV; separation voltage; 16 kV. The other details discussed in the material and methods section.

FIG. 12B shows the chart of CE analysis report of the sequence I.D.#10, sequence dFC GGA GCT GGA ACG, lot #120202sc1119a, with the listings of the peaks observed, their migration time in minutes, area percent.

FIG. 13: Flow cytometric DNA cell cycle profiles: Effect of GEMCITABINE-ODN's on colon cancer cells, showing GEMCITABINE-ODNs, killing colon cancer cells HT29 much more effectively than by treatment with GEMCITABINE alone, at equivalent dosages. Cells were treated in culture with respective drugs for 1 hour at the stated dosage, and re incubated in normal medium without drugs for a further 47 hours. Column A is treatment by GEMCITABINE (GEMZAR) alone at 20 ng/ml and 50 ng/ml. column B is the treatment with GEMCITABINE-ODN-Seq. I.D.#7, column C is the treatment with GEMCITABINE-ODN-Seq. I.D.#8, column D is the treatment with GEMCITABINE-ODN-Seq. I.D.#9, column E is the treatment with GEMCITABINE-ODN-Seq. I.D.#10, at equivalent GEMCITABINE dosages, at 20 ng/ml and 50 ng/ml of each of the four sequences.

FIG. 14: Flow cytometric DNA cell cycle profiles: Effect of Gemcitabine-ODN's on colon normal cells CCD-112CO, showing Gemcitabine-ODNs killing colon normal cells CCD-112CO more effectively than by treatment with GEMCITABINE alone, at equivalent dosages. Cells were treated in culture with respective drugs for 1 hour at the stated dosage, and reincubated in normal medium without drugs for a further 47 hours. Column A is treatment by Gemcitabine (Gemzar) alone. Column A is treatment by GEMCITABINE (GEMZAR) alone at 20 ng/ml and 50 ng/ml. column B is the treatment with GEMCITABINE-ODN-Seq. I.D.#7, column C is the treatment with GEMCITABINE-ODN-Seq. I.D.#8, column D is the treatment with GEMCITABINE-ODN-Seq. I.D.#9, column E is the treatment with GEMCITABINE- ODN-Seq. I.D.#10, at equivalent GEMCITABINE dosages, at 20 ng/ml and 50 ng/ml of each of the four sequences.

DETAILED DESCRIPTION OF THE INVENTION

All references listed herein are hereby incorporated by reference. Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Lower case symbols shall be equivalent to the same symbols in upper-case. The term "comprises" means "includes." It is further to be understood that all molecular weight or molecular mass values, given for nucleic acids are provided for description. Although methods and materials similar or equivalent to those described herein can be used in the practice or testing of the present invention, suitable methods and materials are described below. In case of conflict, the present specification, including explanations of terms, will control. In addition, the materials, methods, and examples are illustrative only and not intended to be limiting.

In order to facilitate review of the various embodiments of the invention, the following explanations of specific terms are provided:

A "CpG moiety" is a cytosine, guanosine dinucleotide. The C and G are linked together by a natural or modified phosphate backbone, as defined below.

A CGn*CG is a moiety having two or more CG dinucleotides that are intervened by one or more nucleotides.

A "modified phosphate" is a phosphate group of the formula R—P=O that is part of the internucleotide linkage between two nucleotides. Examples of modified phosphates of the invention include natural phosphodiester (R=OH), alkoxy phosphotriester (R is a lower alkoxy containing 1 to 6 carbon atoms such as $OCH_3$, $OC_2H_5$, n-$OC_3H_7$, that is, a straight chain n-$OC_3H_7$, or iso-$OC_3H_7$), a substituted lower alkoxy, such as 1-6 carbon, as set forth in U.S. Pat. No. 5,023,243 and European Patent No. 0 092 574, both of which are incorporated by reference), phosphorothioate, (R=S; i.e., one of the non-bridging oxygens is replaced with sulfur, as set forth in International Patent Application WO 95/26204, herein incorporated by reference), and phosphoramidate (R=NH, as described in U.S. Pat. No. 4,469,863, which is incorporated herein by reference), and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. and Peyman, A. Chem. Rev. 90:544, 1990; Goodchild, J. Bioconjugate Chem. 1:165, 1990. All references cited are incorporated herein by reference.).

The oligonucleotide may also be a chimera derived from natural and modified deoxy, ribo and 2'-modified nucleoside bases.

"N-Bz" refers to the amine-protecting group benzoyl attached to a nitrogen.

The abbreviation "ODN" refers to oligodeoxynucleotides.

An "oligonucleotide" or "oligo" shall mean multiple nucleotides (i.e. molecules comprising a sugar (e.g. ribose or deoxyribose) linked to a phosphate or modified phosphate group and to an exchangeable organic base, which is either a substituted pyrimidine (such as, cytosine (C), thymine (T) or uracil (U)), or a substituted purine (such as, adenine (A) or guanine (G)). In one embodiment, the invention provides an oligonucleotide with modified or uncommon bases, such as inosine, 5-methylcytosine, 5-azacytosine, 5-halogen substituted (F, Cl, Br, I) uracil or cytosine, and 5-alkyl substituted uracil or cytosine, such as C-5 propyne uracil and C-5 propyne cytosine. Purine modification includes 7-deazaadenine, 7-deazaguanine, 7-iodo-7-deaza adenine, 7-iodo-7-deaza-guanine, 7-propyne-7-deaza adenine, and 7-propyne-7-deazaguanine. Other such modifications are well known to the skilled artisan.

The sugar and bases of one or more nucleotides that make up the oligonucleotide may have one or more substitutions. Examples include one or more nucleotides having a 2'-O-alkyl, 2'-N-alkyl, or 2'-halogen modifications on the sugar. Preferably the alkyl is a $C_1$-$C_6$ alkyl.

Oligonucleotides may include one or more protecting groups for stability during oligonucleotide synthesis or in vivo conditions.

Oligonucleotides can be obtained from existing nucleic acid sources (e.g. genomic or cDNA), but are preferably synthetic, and have a defined sequence (e.g. produced by oligonucleotide synthesis).

An "oligonucleotide delivery complex" is an oligonucleotide associated with (e.g. ionically or covalently bound to; or encapsulated within) a targeting means (e.g. a molecule that results in a higher affinity binding to a target cell, such as that of a B-cell or natural killer (NK) cell, and/or increased cellular uptake by target cells). Examples of oligonucleotide delivery complexes include oligonucleotides associated with: a sterol (e.g. cholesterol), a lipid (e.g. cationic lipid, virosome or liposome), or a target cell specific binding agent (e.g. a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, J. Immunol. 167: 3324, 2001.)

"Pharmaceutically acceptable carriers" that are useful in this invention are conventional, see for example, *Remington's Pharmaceutical Sciences*, by E. W. Martin, Mack Publishing Co., Easton, Pa., 15th Edition (1975), which is incorporated herein by reference.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, such as sodium acetate or sorbitan monolaurate.

As used herein, the term "protecting group" includes groups that protect reactive sites that need to be deprotected and treated with further reagents and activated monomers during the course of oligomerization, such as a 5'-hydroxyl groups. This term is meant to include groups that block reactive sites during oligomerization reactions, and are stable during oligonucleotide synthesis conditions. Such groups are removed by treatment with a deblocking agent after the oligomerization is complete thus allowing the incorporation of a variety of reactive functionalities at specific sites throughout the final oligomeric compound. U.S. Pat. No. 6,649,750 discloses the use of protecting groups in oligonucleotide synthesis, and is incorporated herein by reference. Representative protecting groups are disclosed by Beaucage, S. L.; Uyer, R. P., Advances in the Synthesis of Oligonucleotides by the Phosphoramidite Approach, Tetrahedron, 48: 2223-2311, 1992, which is incorporated herein by reference. Deprotection techniques are well known in the art, (See Padmapriya et al., Antisense Res. & Dev. 4: 185-199, 1994.), which is incorporated herein by reference.

A "prodrug" is a moiety of the oligonucleotide that can be hydrolyzed to form a purine or pyrimidine antimetabolite. In some embodiments, the antimetabolite is selected from the group consisting of 2'-deoxy, 2',2'-difluorcytidine, 2'-deoxy-3'-thiacytidine, 3'-azido-3'-deoxythymidine, 2',3'-dideoxycytidine, 2',3'-didehydro-3'-deoxythymidine, 2',3'-dideoxyinosine, 5-fluoro-2'-deoxy uridine, 2-fluoro-9-b-D-arabinofuranosyladenine, 1-B-D-arabinofuranosylcytosine, 5-azacytidine, 5-aza-2'-deoxycytidine, 6-mercaptopurineribo side, 2-chlorodeoxyadeno sine, and pentostatin. To obtain the antimetabolite, the linkage(s) between the prodrug and other nucleotide(s) of the oligonucleotide is hydrolyzed by natural or non-naturally occurring enzymes to obtain an antimetabolite nucleoside. In additional embodiments, hydroxyl-protecting groups (e.g., dimethoxytritryl, monomethoxytrityl, trimethoxytrityl, 9-fluorenyl carbonyl, tetrahydropyranyl, benzoyl, phenoxyacetyl, acetyl, propyl, butyryl, isobutyryl, or other higher homologs) also need to be removed by a deblocking agent in order to obtain the antimetabolite. In some embodiments, amine-protecting groups (e.g., benzoyl, acetyl, propyl, butyryl, isobutryl, phenoxy acetyl, substituted phenoxy acetyl, 9-fluorenyl carbonyl, also need to be removed by hydrolysis to obtain the antimetabolite. Antimetabolites kill both cancer and non-cancerous cells at about the same rate. This invention is based on the finding that oligonucleotides that include at least two CpG moieties and at least one prodrug of an antimetabolite preferentially kill cancerous cells. The oligonucleotide may have one or more ribonucleotides and/or one or more deoxyribonucleotides.

Thus, in one embodiment, the invention provides an oligonucleotide for preferentially killing cancerous cells over non-cancerous cells. The oligonucleotide includes at least two CpG moieties and a prodrug for an antimetabolite covalently linked to the oligonucleotide. The prodrug is a prodrug for a cancer-fighting antimetabolite. Known cancer-fighting antimetabolites include 2'-deoxy-3'-thiacytidine, 3'-azido-3'-deoxythymidine, 2',3'-dideoxycytidine, 2',3'-didehydro-3'-deoxythymidine, 2',3'-dideoxyinosine, 5-fluoro-2'-deoxy uridine, 2-fluoro-9-b-D-arabinofuranosyladenine, 1-B-D-arabinofuranosylcytosine, 5-azacytidine, 5-aza-2'-deoxycytidine, 6-mercaptopurineriboside, 2-chlorodeoxyadenosine, and pentostatin. Preferably, the antimetabolite is 2'-deoxy, 2',2'-difluorocytidine.

Preferably, the at least two CpG moieties are separated by 2, 5, or 9 nucleotides. The nucleotides between the CpG moieties may be naturally or non-naturally occurring nucleotides, or a combination of the two.

In one embodiment, the oligonucleotide has between about 4 and about 50 nucleotides. In another embodiment, an oligonucleotide having between about 10 and about 40 nucleotides is provided by the invention. In yet another embodiment, the invention provides an oligonucleotide having between about 20 and about 30 nucleotides. More preferably, the oligonucleotide is between about 10 and about 20 nucleotides long. Most preferably, the prodrug is a prodrug for the antimetabolite 2'-deoxy, 2',2'-difluorocytidine.

As described above, the oligonucleotide has at least two CpG moieties. The CpG moieties are interspersed throughout the oligonucleotide. If there are only two CpG moieties in the oligonucleotide sequence, they are most preferably 2, 5 or 9 nucleotides apart. If there are more than two CpG moieties in the oligonucleotide sequence, preferably two of the more than two CpG moieties are 2, 5 or 9 nucleotides apart. The invention further includes oligonucleotides with other spacings between the two or more CpG moieties.

The prodrug, which is generally a modified nucleotide, may be incorporated within the oligonucleotide at any position. Thus, it may be at the 5' end, at the 3' end, or at an internal position of the oligonucleotide. It may be one or more nucleotides 5' or 3' to the at least two CPG moieties, including directly adjacent to a CPG moiety. Alternately, it may be one or more nucleotides 5' to one or more CPG moieties and one or more nucleotides 3' to one or more other CPG moieties.

Thus, in one embodiment, the prodrug is at a position that is between 1 and about 10 nucleotides upstream from one of the at least two CpG moieties. In another embodiment, the prodrug is between 1 and about 10 nucleotides downstream from a CpG moiety.

In some embodiments, one of the nucleotides in one of the CpG moieties is the prodrug antimetabolite. For example, the invention provides the following compositions, in which the notation "dFC" refers to the prodrug for 2'-deoxy, 2',2'-difluorocytidine:

```
dFC GN NCG dFC GN NNN NCG dFC GNN NNN NNN NCG dFC GNN CGN NNN NCG

NNN dFC GN NCG

NNN dFC GN NNN NCG

NNN dFC GNN NNN NNN NCG

NNN dFC GNN CGN NNN NCG
```

In other words, the prodrug of the antimetabolite replaces one of the nucleotides in at least one of the at least two CpG moieties. In general the prodrug replaces the natural base, from which it is derived. Thus, the oligonucleotide has a motif represented by the formula: 5'PGXCG3' in which P is a prodrug for an antimetabolite and X represents a number of nucleotides in the range of 0-50, and preferably 2, 5, or 9. Preferably, the prodrug for 2'-deoxy, 2',2'-difluorocytidine replaces a cytosine in one of the CpG moieties. Most preferably, the antimetabolite is 2'-deoxy, 2',2'-difluorocytidine and is the most 5' nucleotide of oligonucleotide.

The oligonucleotides of the invention may also have modifications that are not normally found in nature or that are found in nature in small quantities. In one embodiment, the invention provides an oligonucleotide having at least one nucleotide having a 2'-O-alkyl modification on the sugar of at least one nucleotide. Examples of alkyls include methyl, ethyl, propyl, ethenyl, and higher homologs. Preferably, the homolog has no more than 6 carbon atoms. Most preferably, the alkyl is methyl. In another embodiment, the invention provides an oligonucleotide having at least one 2'-N-alkyl modification. In yet another embodiment, the invention provides an oligonucleotide having at least one 2'-halogen modification.

In one embodiment, the prodrug is attached to the oligonucleotide by a 3'-3' linkage. In another embodiment, the prodrug is attached to the oligonucleotide by a 5'-5' linkage. These types of chemical modifications are known to the skilled person and are described, for example, in M. Koga et al., J. Org. Chem. 56:3757, 1991, EP 0 464 638, and EP 0 593 901, U.S. Pat. No. 5,750,669, each of which is incorporated herein by reference. The synthesis of an oligonucleotide having a 3'-3' linkage at the 3' end can be achieved by attaching the 5' end of a nucleoside attached to a solid support; this nucleoside then will allow growth of an oligonucleotide from the 3' end. Similarly, the synthesis of an oligonucleotide having a nucleotide linked by a 5'-5' linkage at the 5' end of the oligonucleotide can be achieved by using a nucleotide having a support attached at the 3' end that will allow growth of the oligo from the 5'-end.

The prodrug may also be linked by a 3'-5' linkage or a 5'-3' linkage, both of which are well known to the skilled artisan. Attachment of a prodrug to the oligo via a linker, will cause liberation of the prodrug at the cancer cell sites by hydrolytic enzymes and will have the effect of the prodrug as well as the CGn*CG (SEQ ID NO: 3) oligonucleotide. An example of a point of cleavage between a prodrug and the oligonucleotide is an ester linkage. The aliphatic esters are chosen for this purpose, since they are stable, yet can be easily hydrolyzed inside cells by intracellular esterases. Aliphatic phosphate esters, alkyl substituted phosphate esters, and amidates are also part of this discovery, since they are also hydrolyzed by intracellular enzymes. Aliphatic amide linkages are chosen at the other side of linkage. The amide linkage is generally required in order to attach the prodrug and oligonucleotide. Thus, one end bears a carboxylic or activated ester of carboxylic acid, and the other end has a free amino function, to effect the joining of two moieties. This approach is extensively used in oligonucleotide labeling with various chromophores and ligands (See, P. S. Nelson, M. Kent and Sylvester Muthini, Nucleic Acids Research, Vol. 20, No. 23: 6253-6259, 1992; Misiura, K., Durrant, I., Evans, M. R., and Gait, M., Nucleic Acids Research, Vol., 18: 4345-4354, 1990; Zendegui, J. G., Vasquez, K. M., Tinsley, J. H., Kessler, D. J. and Hogan, M. E., Nucleic Acids Research, Vol. 20: 307-314, 1992. Each of these is incorporated herein by reference.).

Exemplary oligonucleotides within the scope of the invention are shown in Formulas I-XI. Each of these includes at least two CpG motifs. These oligonucleotides should not be used to limit the scope of the invention. In some embodiments, the prodrug replaces one of the nucleotides of one of the CpG motifs. In other embodiments, the prodrug does not replace one of the nucleotides of the CpG motifs.

Each of these formulas shows oligonucleotides that include the prodrug of the antimetabolite 2'-deoxy, 2',2'-difluorocytidine. Oligonucleotides with prodrugs for other antimetabolites may be used within the scope of the invention in the same position as shown for 2'-deoxy, 2',2'-difluorocytidine or in other positions. Intermediates useful in the synthesis of these oligonucleotides are described below as well. Oligonucleotides of the invention may further include one or more protecting groups as defined herein.

For formulas I through XI, the subsequent symbols are used to mean the following:

C represents cytosine or a modified cytosine including: a 5-alkyl cytosine such as 5-methyl cytosine, a 5-alkenyl homolog, a 5-alkynyl homolog, or a 5-halogen analog. The nucleotide with the C base is the prodrug for 2'-deoxy, 2',2'-difluorocytidine. In another embodiment, the nucleotide with the C base is an analog of 2'-deoxy, 2',2'-difluorocytidine.

The phosphodiester bond is selected from a natural phosphodiester (R=H), alkoxy phosphotriester (R is a lower alkoxy containing 1 to 6 carbon atoms such as $OCH_3$, $OC_2H_5$, n-$OC_3H_7$, iso-$OC_3H_7$, a substituted lower alkoxy, such as $OCH_2OCH_3$, phosphorothioate (R=S), a straight or branched $C_1$-$C_6$ alkyl, and phosphoramidate (R=NH). Other internucleotide linkages may be used within the context of the invention.

B, B' and B" are the same or different natural or modified bases. Natural bases include adenine, cytosine, guanine, thymine, inosine, and uridine. Modified bases include 5-methylcytosine, 5-azacytosine, 5-halogen substituted (F, Cl, Br, I) uracil or cytosine, and 5-alkyl substituted uracil or cytosine, such as, C-5 propyne uracil and C-5 propyne cytosine. Purine modifications can include 7-deazaadenine, 7-deazaguanine, 7-iodo-7-deaza adenine, 7-iodo-7-deazaguanine, 7-propyne-7-deazaadenine, 7-propyne-7-deazaguanine. Other bases are well known to the skilled artisan. The repeating portion of the oligonucleotide may have the same or different bases, and the term B' should not be construed to imply that the same nucleotide is repeated n number of times, but rather that there are n nucleotides each of which has a base that is within the definition of B'.

N is 2 to 50.

S stands for fluorine, chlorine, a sulfur derivative (i.e., S-alkyl), or a nitrogen with alkyl groups (i.e., N—R', R", in which R' and R" are the same or different alkyl groups with up to 8 carbon atoms).

Formula I

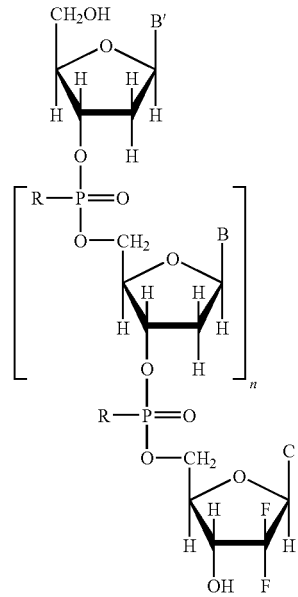

In one embodiment (Formula I), the prodrug is attached at the 3'-end of an oligonucleotide via a 3'-5' linkage.

In another embodiment, the invention provides the oligonucleotide shown in Formula II. In this case, the prodrug is attached at the 5'-end of the oligonucleotide via a 5'-5'-Linkage. The oligonucleotide can be synthesized with a prodrug phosphoramidite, in which the phosphoramidite is at the 5' of the oligonucleotide.

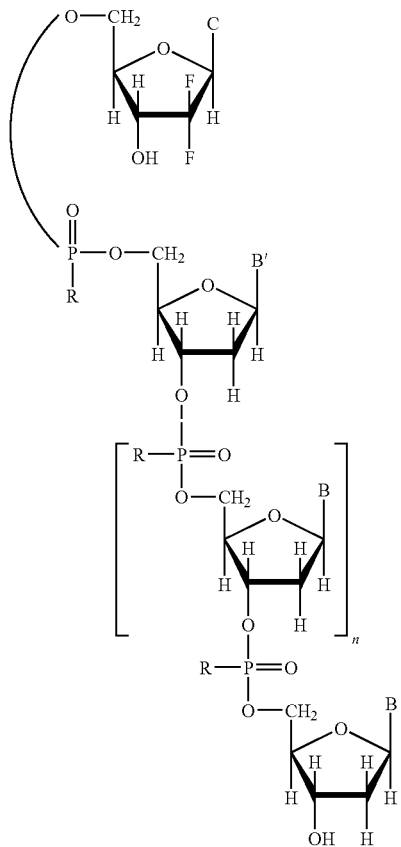

Formula II

In another embodiment, the invention provides an oligonucleotide of the following formula:

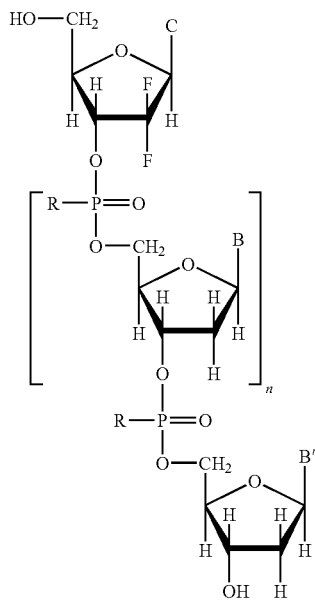

Formula III

The prodrug is attached at the 5'-end of the oligonucleotide via a 3'-5'-linkage.

In another embodiment, the invention provides an oligonucleotide of the following formula:

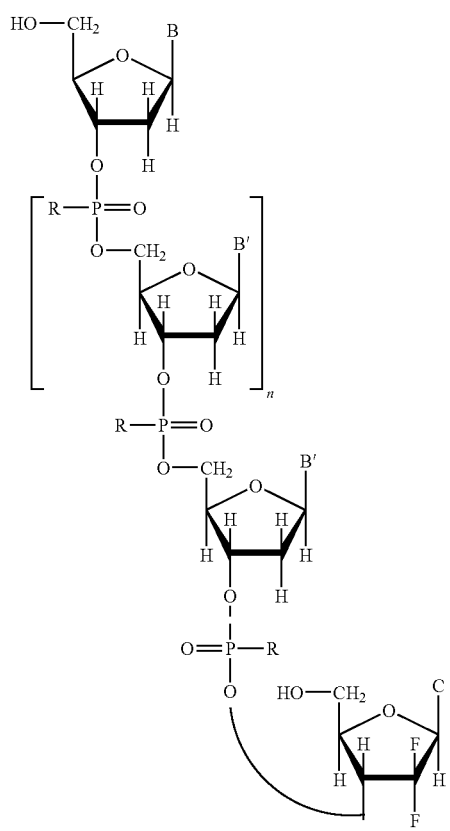

Formula IV

The prodrug is attached at the 3'-end of the oligonucleotide via a 3'-3'-linkage.

In yet another embodiment, the invention provides the oligonucleotide shown in Formula V.

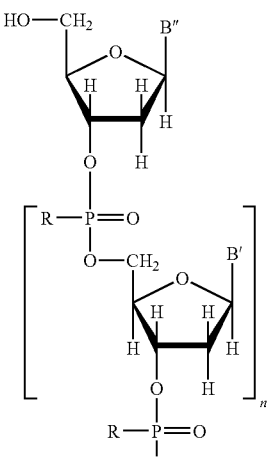

FORMULA V

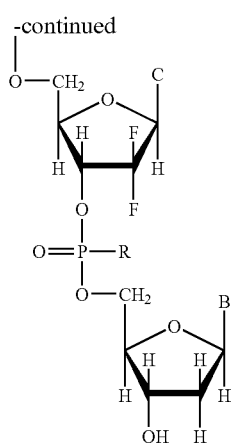

In this embodiment, the prodrug is at an internal position of the oligonucleotide. The synthesis of such an oligonucleotide can be achieved by the use of a phosphoramidite nucleotide of the prodrug using well-known oligonucleotide synthesis techniques.

The invention further provides an oligonucleotide having the following formula:

Formula VI

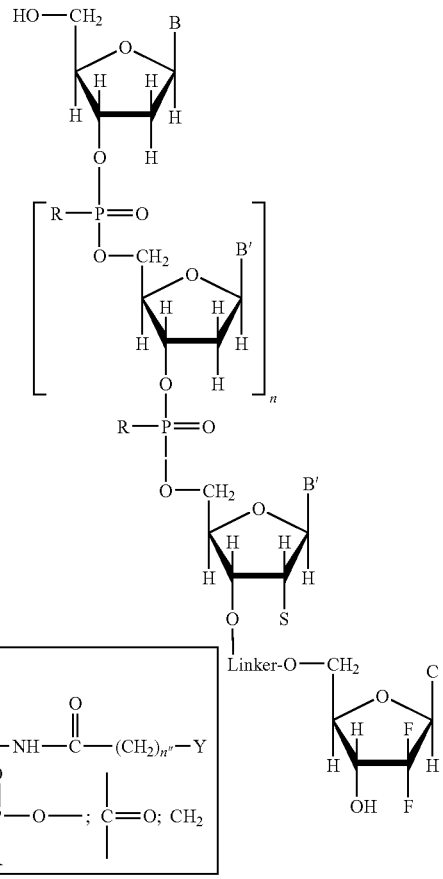

In this embodiment, the prodrug is attached to the 3'-end of an oligonucleotide via a lipophilic ester group at the prodrug's 5'-position. "X, Y=" means that X and Y are independently chosen from the three groups shown. The coupling could be done with an amino linker oligonucleotide. The amino linker oligonucleotides having various spacer lengths are well known in the oligonucleotide chemistry. (See, P. S. Nelson, M. Kent, S. Muthini, Nucleic Acids Research, Vol. 20, No. 23: 6253-6259, 1992; F. Berg, D. Praseuth, A. Zerial, N. Thoung, U. Asseline, T. Le Doan, C. Helene, Nucleic Acids Research, 18: 2901-2908, 1990, which are hereby incorporated by reference.)

Suitable ester groups include carboxylic ester, methylene and phosphate ester groups. The assembly of oligonucleotides having a lipophilic ester is well known to the skilled artisan. For example, if the prodrug is 2'-deoxy, 2',2'-difluorocytidine, the oligonucleotide can be synthesized using the 2',2'-difluorocytidineactive ester, an example of which is shown in formula XVIII. The oligonucleotide in this case will have a 3'-amino linker, which is well known in the art. The final oligonucleotide as depicted in Formula VII will be formed from the reaction of 3'-amino linker oligonucleotide and the active ester of formula XVII.

In another embodiment, the invention provides an oligonucleotide of the following formula:

FORMULA VII

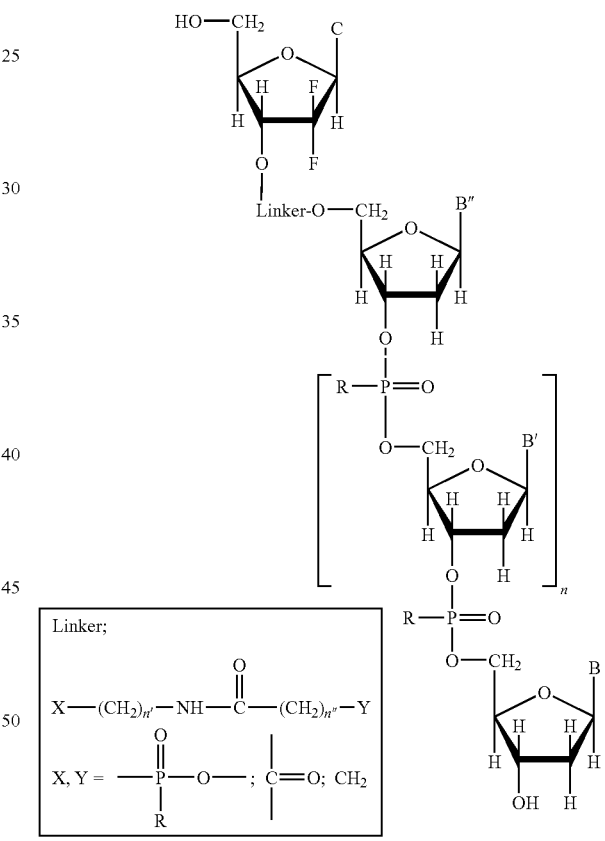

In this oligonucleotide, the prodrug is attached via a linker, at its 3'-position to the 5'-end of an oligonucleotide. The synthesis of oligonucleotides having a lipophilic group can be accomplished by procedures cited in the literature, e.g., (Nikolai N. Polushin and Jack Cohen, Nucl. Acids Res., 22: 5492-5496, 1995). One such procedure will require the prodrug attached to solid support at the 5'-end, which will subsequently be treated with an amino linker at the 3'-end. The 3'-amino linker prodrug can then be coupled with an oligonucleotide having a carboxylic linker at its 5'-end. The general synthesis of oligonucleotide having a 5'-aliphatic carboxylic group can be derived from commercially available products, such as DMT-Thymidine-succinyl hexamide amidite, which is available from ChemGenes Corporation, Wilmington, Mass., catalog item number CLP-2244.

In yet another embodiment, the invention provides an oligonucleotide of the following formula:

Formula VIII

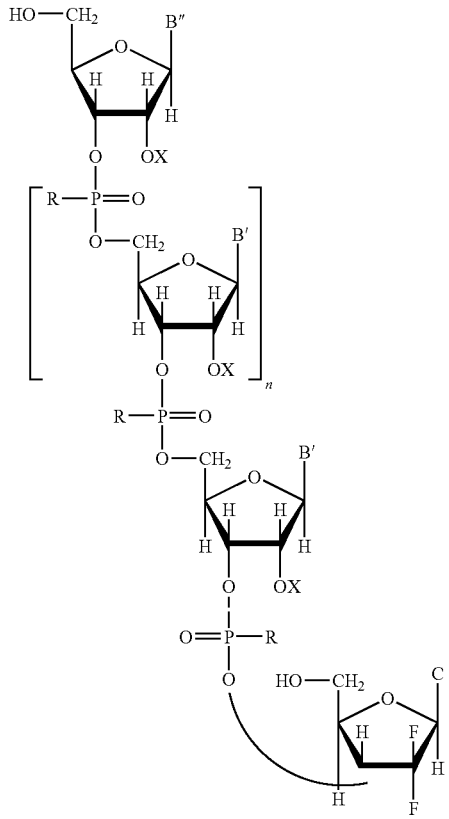

In this embodiment, the prodrug is attached at the 3' end of an RNA or a 2'-modified RNA oligonucleotide, via a 3'-3' linkage. The X stands for H, methyl, ethyl, a higher $C_3$-$C_6$ alkyl homolog, a $C_2$-$C_6$ alkenyl, a $C_2$-$C_6$ straight or branched alkynyl, an amino $C_1$-$C_6$ alkyl, an amino $C_2$-$C_6$ alkenyl, cyclopropyl, an allyl, a $C_1$-$C_6$ alkynylalkoxy, or an aminoalkoxy.

In yet another embodiment, the invention provides oligonucleotides of the following formula:

Formula IX

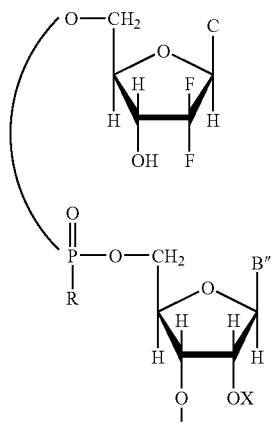

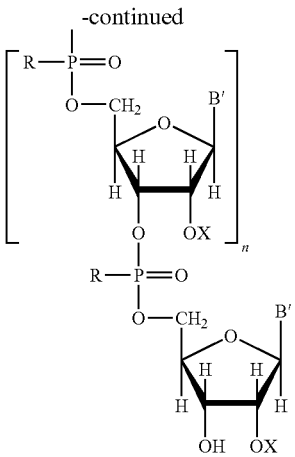

X is defined as used for Formula VII. Such oligonucleotides have a prodrug attached via a 5'-5'linkage at the 5' end of an RNA or a 2'-modified RNA. The attachment of a prod rug via its 5'-end can be achieved using a prodrug phosphoramidite, for example, the prodrug that is depicted in formula XX. The X is used as defined in reference to Formula VIII.

In yet another embodiment, the invention provides an oligonucleotide of the following formula:

Formula X

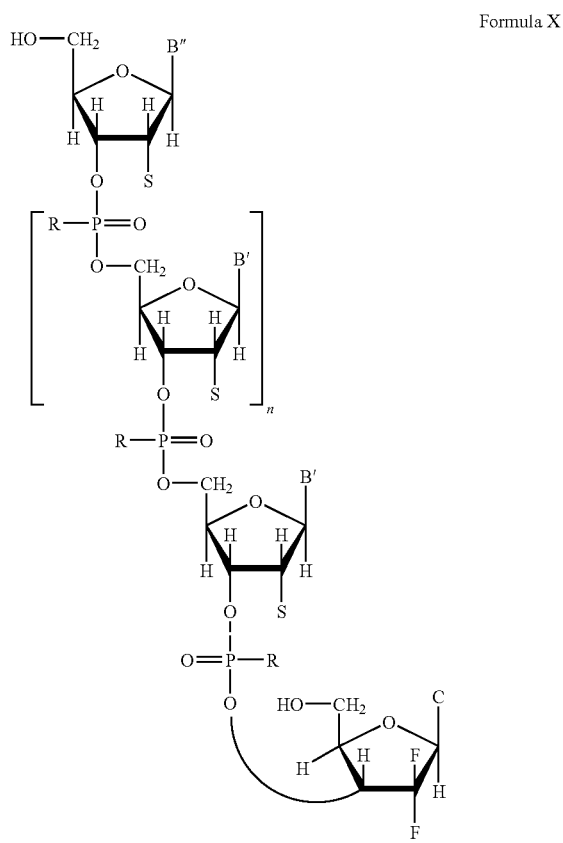

In this embodiment, the prodrug is attached at its 3' end to the 3'-end of an RNA or a 2'-modified RNA oligonucleotide. The attachment of the prodrug at its 3'-end can be achieved using the prodrug bound to a solid support at its 5'-end, as depicted in formula XV for the prodrug of 2'-deoxy, 2',2'-difluorocytidine.

In yet another embodiment, the invention provides an oligonucleotide of the following formula:

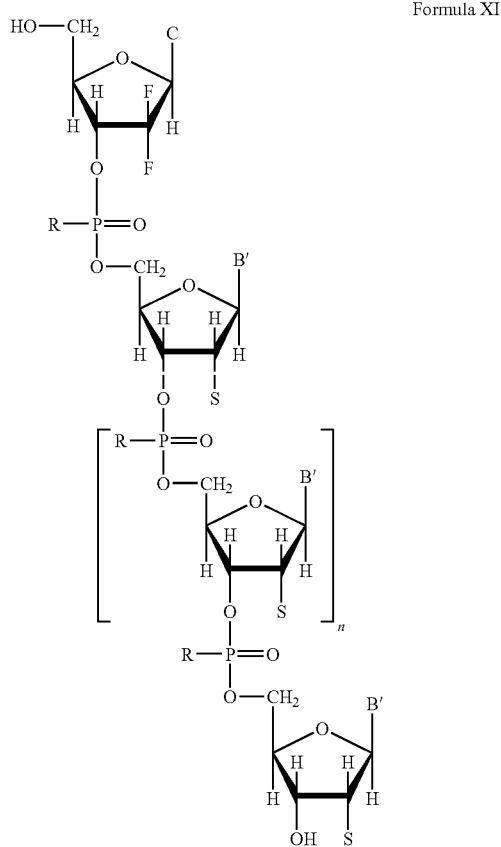

Formula XI

Here, the prodrug is attached at its 3' end to the 5'-end of an RNA or a 2'-modified RNA.

Oligonucleotides can be synthesized de novo using any of a number of procedures well known in the art. For example, the β-cyanoethyl phosphoramidite method (S. L. Beaucage and M. H. Caruthers, Tet. Let. 22:1859, 1981; U.S. Pat. Nos. 4,415,732 and 4,458,066, (Caruthers), and U.S. Pat. No. Re 34,069, (Koster)) the nucleoside H-phosphonate method (Garegg et al., Tet. Let. 27: 4051-4054, 1986; Froehler et al., Nucl. Acid. Res 14: 5399-5407, 1986; Garegg eg al., Tet. Let. 27: 4055-4058, 1986; Gaffney et al., Tet. Let. 29: 2619-2622, 1988) can be used to synthesize oligonucleotides of the invention. Each of the above references is hereby incorporated by reference. These chemistries can be performed by a variety of automated oligonucleotide synthesizers available in the market. The oligonucleotides used in accordance with this invention may be conveniently and routinely made through the well-known technique of solid phase synthesis. Equipment for such synthesis is sold by several vendors including Applied Biosystems (Foster City, Calif.). It is also well known to use similar techniques to prepare other oligonucleotides such as phosphorothioates or alkylated derivatives. It is also well known to use similar techniques and commercially available modified phosphoramidites and solid supports, such as polystyrene, various silica gels in beads or powder forms, and controlled-pore glass (CPG) products to synthesize naturally-occurring and modified oligonucleotides. An example of use of a solid support to synthesize oligonucleotides is provided in U.S. Pat. No. 6,646,118 which is incorporated herein by reference.

In one embodiment, a pharmacological composition is provided that includes an oligonucleotide of the invention and a pharmacologically acceptable carrier. Pharmacologically acceptable carriers (e.g., physiologically or pharmaceutically acceptable carriers) are well known in the art. A suitable pharmacological composition can be formulated to facilitate the use of oligonucleotides in vivo and/or ex vivo. Such a composition can be suitable for delivery of the active ingredient to any suitable host, such as a patient for medical application, and can be manufactured in a manner that is itself known, e.g., by means of conventional mixing, dissolving, granulating, dragee-making, levigating, emulsifying, encapsulating, entrapping or lyophilizing processes.

Pharmacological compositions for use can be formulated in a conventional manner using one or more pharmacologically (e.g., physiologically or pharmaceutically) acceptable carriers comprising excipients, as well as optional auxiliaries that facilitate processing of the active compounds into preparations, which can be used pharmaceutically. Proper formulation is dependent upon the route of administration chosen, and whether use will be an in vivo or an ex vivo use. For use in vivo, administration can be either systemic or local. In addition, one of skill in the art can readily select a suitable route of administration, including, but not limited to, intravenous, intramuscular, intraperitoneal, transmucosal, subcutaneous, transdermal, transnasal, and oral administration.

Thus, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. For administration by inhalation, the active ingredient is conveniently delivered in the form of an aerosol spray presentation from pressurized packs or a nebuliser, with the use of a suitable propellant.

The active ingredient can be formulated for parenteral administration by injection, e.g., by bolus injection or continuous infusion.

Oligonucleotides of the invention can be formulated for intratracheal administration or for inhalation. Such compositions can take such forms as suspensions, solutions or emulsions in oily or aqueous vehicles, and can contain formulatory agents such as suspending, stabilizing and/or dispersing agents. Other pharmacological excipients are known in the art.

Preferably, the pharmaceutically acceptable carrier is lipofectin.

For therapeutic or prophylactic treatment, oligonucleotides are administered in accordance with this invention. Oligonucleotides may be formulated in a pharmaceutical composition, which may include carriers, thickeners, diluents, buffers, preservatives, surface active agents and the like, in addition to the oligonucleotide. Pharmaceutical compositions may also include one or more active ingredients such as antimicrobial agents, anti-inflammatory agents, anesthetics, and the like in addition to oligonucleotides. Conventional chemotherapeutic agents may also be included.

In one embodiment, the oligonucleotides of the invention are included in a delivery complex. The delivery complex can include the oligonucleotide of the invention and a targeting means. Any suitable targeting means can be used. For example, the oligonucleotide of the invention can be associated with (e.g., ionically or covalently bound to, or encapsulated within) a targeting means (e.g., a molecule that results in higher affinity binding to a target cell, such as a B cell). A variety of coupling or cross-linking agents can be used to form the delivery complex, such as protein A, carbodiamide, and N-succinimidyl-3-(2-pyridyldithio) propionate (SPDP). The complex is sufficiently stable in vivo to prevent significant uncoupling prior to delivery to the target cell. In one embodiment, the delivery complex is cleavable such that the oligodeoxynucleotide is released in a functional form at the target cells.

Dosing is dependent on severity and responsiveness of the condition to be treated. Persons of ordinary skill can easily determine optimum dosages, dosing methodologies and repetition rates. Optimum dosages may vary depending on the relative potency of individual oligonucleotides, and can generally be calculated based on in vitro and in vivo animal studies. Thus, in the context of this invention, by "therapeutically effective amount" is meant the amount of the compound required to have a therapeutic effect on the treated mammal. This amount, which will be apparent to the skilled artisan, will depend upon the type of mammal, the age and weight of the mammal, the type of disease to be treated, perhaps even the gender of the mammal, and other factors which are routinely taken into consideration when treating a mammal with a disease. A therapeutic effect is assessed in the mammal by measuring the effect of the compound on the disease state in the animal. For example, in mammals being treated for cancer, therapeutic effects are assessed by measuring the rate of growth or the size of the tumor, or by measuring the production of compounds such as cytokines, which production is an indication of the progress or regression of the tumor.

The invention further provides intermediates that are useful for the synthesis of oligonucleotides of the invention. For Formulas XII-XX, x is an amine-protecting group for the N4 amine as an amide bond, such as a lower (i.e., C1-C6) alkanoyl group containing a straight or a branched chain alkyl group as defined above, an aryl or substituted aryl having a C1-C6 alkyl or halogen as a substituent on the aryl ring, an aroyl having an aryl or substituted aryl group as defined above, a phenoxy acetyl or appropriately protected phenoxy acetyl for fast deprotection, a trifluroacetyl or FMOC group, an imine derivative such as formamidine or dimethylformamidine. Such protecting groups are required in this invention to offer mild and convenient deprotection conditions after the synthesis of the oligonucleotides of the present invention, and can be cleaved with a suitable reagent to generate free NH2 groups at the end of the oligonucleotide synthesis. R is H, a halogen (F, Cl, Br, I), a $C_1$-$C_6$ alkyl, a $C_2$-$C_6$ alkenyl or a $C_2$-$C_6$ alkynyl group. Preferably, R is H. Such modifications and protecting groups on the 4-$NH_2$ group of 2'-deoxy, 2',2'-difluorocytidine are essential to the synthesis of the oligonucleotides of the invention.

In one embodiment the invention relates to 4-$NH_2$ protected derivatives of 2'-deoxy, 2',2'-difluorocytidine which are shown in Formula XII, which is an intermediate for the preparation of various 2'-deoxy, 2',2'-difluorocytidine attached oligonucleotides.

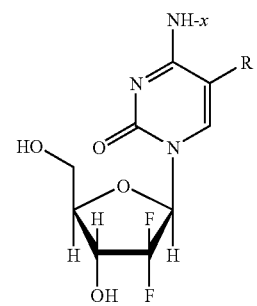

Formula XII

Further embodiments of the invention relate to 5'-OH protected derivatives of 2'-deoxy, 2',2'-difluorocytidine or of the 4-amine protected 2'-deoxy, 2',2'-difluorocytidine. These are useful in intermediates for the preparation of 2'-deoxy, 2',2'-difluorocytidine attached oligonucleotides. These intermediates are shown in Formula XIII.

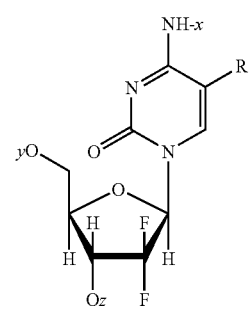

Formula XIII

Y is hydroxyl-protecting group such as DMT (dimethoxytritryl), MMT (monomethoxytrityl), TMT (trimethoxytrityl), FMOC (9-fluorenyl carbonyl chloride), tetrahydropyranyl, benzoyl, phenoxyacetyl, acetyl, propyryl, butyryl, isobutyryl, or other higher homologs. Z is a succinyl (—C(=O) CH$_2$CH$_2$C(=O)—OH, hydroquinolynyl, oxalyl or other related carboxylic groups for attachment to a solid support.

Further embodiments relate to 3'-OH protected derivatives of 2'-deoxy, 2',2'-difluorocytidine or of 4-amine protected 2'-deoxy, 2',2'-difluorocytidine. These are useful as intermediates in the preparation of 2'-deoxy, 2',2'-difluorocytidine attached oligonucleotides.

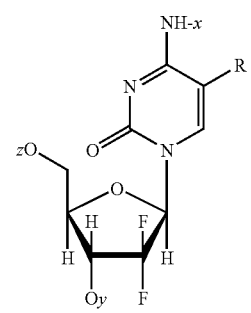

Formula XIV

As for Formula XIII, x is an amine-protecting group. Y is a hydroxyl-protecting group, and Z is as previously defined.

A further embodiment relates to 5'-OH protected derivatives of 2'-deoxy, 2',2'-difluorocytidine (Formula XV) and 3'-OH protected derivatives of 2'-deoxy, 2',2'-difluorocytidine (Formula XV) having succinyl ester, hydroquinolynyl, oxalyl or related esters. These esters can be attached to a solid support for oligonucleotide synthesis.

Y has the formula C(=O)-M-C(=O)—NH-Spacer-Solid Support, where M is succinyl, oxalyl, hydroquinolynyl, or another suitable group which is cleaved after oligonucleotide synthesis. Suitable supports include controlled pore glass, commonly called "CPG", various polystyrenes, and other solid supports amenable to solid phase oligonucleotide synthesis. The Spacer is a C1-C6 alkyl, ethyloxyglycol, a combination of alkyl and ethyleneglycoxy, aromatic, hydroaromatic in nature. Z is a hydroxyl-protecting group as defined above.

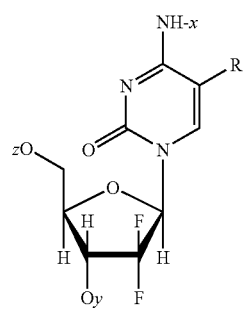

Formula XV

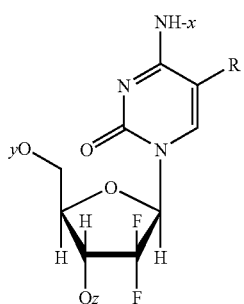

Formula XVI

In yet another embodiment, the invention provides active esters of 2'-deoxy, 2',2'-difluorocytidine at the 5'-position (Formula XVII) and at the 3'-position (Formula XVIII) of the 4-amino protected 2'-deoxy, 2',2'-difluorocytidine. These are useful as intermediates for the preparation of 2'-deoxy, 2',2'-difluorocytidine attached via linker and spacer. Such active esters can be attached to oligonucleotides by coupling with the amino function in the oligonucleotide. The amino linked oligonucleotides are well known in the field of oligonucleotides and they have been routinely used to attach many chromophores and ligands (References cited earlier). Z is a hydroxyl-protecting group. These compounds include an active ester, such as, but not limited to, an n-hydroxysuccinimido function that could be at the 5'-end of 2',2'-difluorocytidine (i.e., Formula XVII) or at the 3'-end (Formula XVII). Q is an aliphatic alkyl $(CH_2)_n$ where n is 1 to 50, or ethylene glycol $(CH_2\ CH_2—O-)_m$ in which m is 1 to 50.

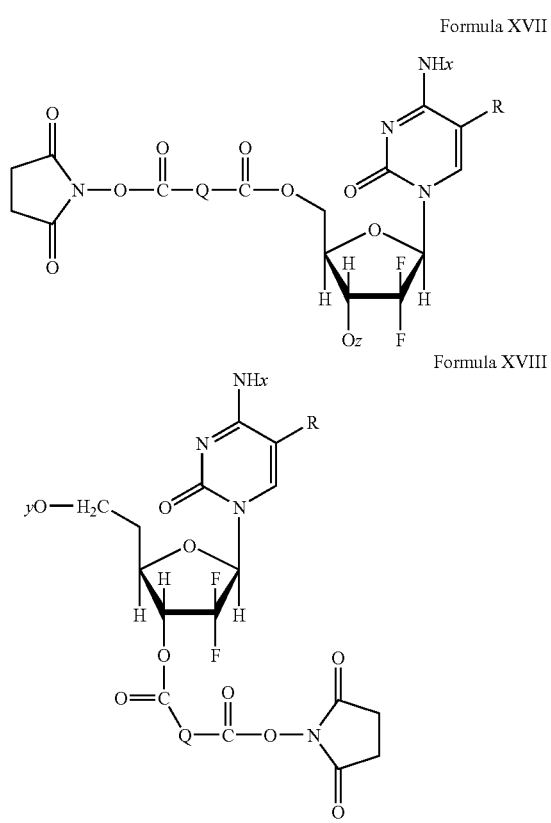

Formula XVII

Formula XVIII

Yet another embodiment relates to 3'-phosphoramidite derivatives of 2'-deoxy-2',2'-difluorocytidine, preferably 2-cyanoethyl-n,n-diisopropylamino phosphoramidite (Formula XIX.). Alternately, the methoxy-n,n-diisopropylaminophosphinyl phosphoramidite group may be used in the place of the 2-cyanoethyl-n,n-diisopropylamino phosphoramidite. These compounds have purity exceeding 97% and have coupling efficiency of greater than 98% in less than 100 seconds under standard DNA/RNA synthesis coupling conditions. The standard coupling conditions are outlined in the DNA/RNA synthesizer manual of MerMade Instrument. The coupling efficiency was monitored by carrying out oligo synthesis in the instrument model, Expedite 8909, and using the built in per step coupling monitor.

Y is a hydroxyl-protecting group as defined above in Formulas XII and XIII, respectively. At the 3'-position, a cyanoethyl phosphoramidite is attached. R' and R" are lower alkyl (straight or branched) groups containing 1 to 6 carbon atoms. Similarly, a methoxy phosphoramidite (in which the cyanoethyl group is replaced by a methoxy group) is within the scope of the invention.

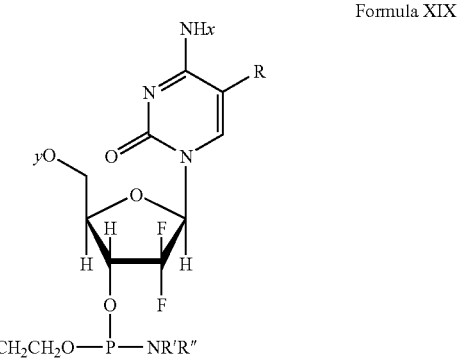

Formula XIX

Formula XX shows a 5' phosphoramidite, in which the symbols X, R, R', R", and Y are used in the same way as in Formula XIX.

Formula XX

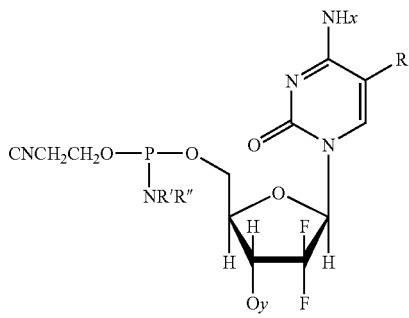

Preferred 2'-deoxy, 2',2'-difluorocytidine derivatives used as intermediates for the preparation of oligonucleotides of the invention are:

N-Benzoyl 2'-deoxy, 2',2'-difluorocytidine

5'-O-DMT (-Benzoyl) 2'-deoxy, 2',2'-difluorocytidine

5'-O-DMT-(N-Benzoyl) 2'-deoxy, 2',2'-difluorocytidine 3'-2-Cyanoethylphosphoramidite

EXPERIMENTAL

Examples

Example I

Preparation of N-Benzoyl-2'-deoxy, 2',2'-difluorocytidine (Compound II)

2'-deoxy, 2',2'-difluorocytidine hydrochloride CAS#95058-81-4; GEMZAR) (Compound I; 2.0 gm), a product of Lilly France, S. A. Fegersheim, France, was dried by coevaporating it twice with 10 ml of dry pyridine. The compound was dissolved in 40 ml of dry distilled pyridine and 57.3 mmole (7.28 ml) of Trimethyl Chloro Silane was then added dropwise at 0° C. under Argon atmosphere. The reaction mixture was brought to 30° C. and was stirred for half an hour. It was then cooled to 0° C. and 10.1 mmole (1.18 ml) of Benzoyl Chloride was added dropwise under argon atmosphere and the mixture was stirred at 30° C. for 2.5 hours. Next, the reaction mixture was cooled to 0° C. and 10 ml of distilled water was added and the diluted mixture was stirred for 10 minutes to quench any excess Trimethyl Chloro Silane and Benzoyl Chloride. Afterwards, 14 ml of precooled ammonium hydroxide solution (28%) was added at 0° C. and stirred for 15 minutes. The solution was then evaporated under high vacuum to gum. The gum was purified on silica gel column (mesh size 70-230) using chloroform and a gradient system consisting of 5-10% methanol in chloroform. The pure product was pooled and dried. The yield was 95%. TLC $R_f$ of compound II, 0.55 in chloroform:methanol in a ratio of 90:10, HPLC analysis showed a sharp single peak $R_t$, 3.9' (system x). UV (methanol) λ max (nm) 261 (ε 17,969) ratio 250/260; 0.766, 260/280; 2.179 $^1$H NMR (CD$_3$OD): 8.41-8.43 (d, 1, H$_6$), 8.01-8.02 (d, 1, H$_5$), 7.44-7.64 (m, 5, Aroma), 6.27-6.30 (t, 1, H1') 4.30-4.34 (m, 1, H3'), 4.00 (br.d, 1, H4'), 3.81-3.84 (qt, 1, H5'), 3.97-3.99 (qt, 1, H5")

Example II

Preparation of 5'-O-DMT (N-Bz) 2'-deoxy, 2',2'-difluorocytidine (Compound III)

The above compound II was taken (3.25 mmole) in dry pyridine and evaporated twice under high vacuum. The residue gum was taken in dry pyridine 12 ml and to the solution was added DMT-Cl (3.6 mmole) at 5° C. The reaction mixture was stirred for 4-5 hours at 5° C. The mixture was then quenched at 0° C. with 20% aqueous pyridine. The total mixture was dried under vacuum. The gum was extracted with chloroform washed with saturated aqueous sodium bicarbonate once, followed by saturated aqueous sodium chloride solution, and evaporation of the solvent on a rotary evaporator. The residue was purified on a silica gel column using chloroform and a gradient system consisting of 2-6% methanol in chloroform. The pure fractions were pooled and dried. The yield of pure compound was 85%. TLC $R_f$ of the compound III, 0.50 in chloroform, hexane, acetone, methanol in a ratio of 50:28:20:2. HPLC analysis showed sharp single peak $R_t$, 6.5' (system y). UV (methanol) λ max (nm) 261 (ε 23,249) ratio 250/260; 0.929; 260/280; 1.875

$^1$H NMR (CDCl$_3$): 8.59-8.60 (br.d, 1, N$^4$H), 8.20-8.21 (d, 1, H$_6$), 7.84-7.86 (d, 1, H$_5$), 6.86-7.72 (m, 18, Aroma), 6.41-6.44 (qt, 1, H1'), 4.46-4.52 (m, 1, H3'), 4.09-4.10 (qt., 1, H4'), 3.81 (s, 6, OCH$_3$), 3.63-3.65 (qt, 1, H5'), 3.52-3.55 (qt, 1, H5")

Example III

Preparation of 5'-O-DMT (N-Bz)-2'-deoxy, 2',2'-difluorocytidine-3'-Cyanoethylphosphoramidite (Compound IV)

Compound III (1.5 mmole) was thoroughly dried with dry acetonitrile and taken up in dry tetrahydrofuran. To the stirred solution was added N,N-diisopropyl ethylamine (3.75 mmole) under argon; the solution maintained at 5° C. N,N-diisopropylamino cyanoethyl phosphoramidic chloride (1.65 mmole) was added dropwise, followed by further reaction at 25° C. for one hour. The reaction mixture was diluted with ethylacetate and washed with saturated aqueous sodium bicarbonate once, followed by saturated sodium chloride once. The organic layer was dried over anhydrous sodium sulfate, followed by evaporation under vacuum. The residue was purified by column chromatography. The solvent system for column and TLC was ethylacetate, hexane and triethylamine in a ratio of 50:40:10. The TLC $R_f$ of compound IV, 0.45 & 0.55. HPLC analysis showed sharp doublets, $R_t$, 3.85' & 4.45' (system z). WV (methanol) λ max (nm) 262 (ε 23,240) ratio 250/260; 0.886; 260/280; 1.749

$^1$H NMR (CDCl$_3$): 8.7 (br.s, 1, N$^4$H), 8.14 & 8.26 (dd, 1, H$_6$), 7.87-7.89 (bd, 1, H$_5$), 6.85-7.62 (m, 18, Aroma), 6.41-6.44 (m, 1, H1'), 4.51-4.72 (dm, 1, H3'), 4.15-4.17 (dm, 1, H4'), 3.80-3.88 (m, 1, POCH$_2$), 3.82-3.83 (d, 6, OCH$_3$), 3.65-3.73 (m, 1, POCH$_2$), 3.53-3.62 (m, 2, H5' and H5"), 3.44-3.50 (m, 2, (Me$_2$CH)$_2$N), 2.35-2.61 (dt, 2, CH$_3$CN), 1.14-1.18 (m, 12, [(CH$_3$)$_2$C]$_2$N). 31 P NMR (CDCL3) lambda 153.351, lambda 155.186, delta 1.835

Example IV

Stability Studies

The 2'-deoxy, 2',2'-difluorocytidine derivatives, N-Bz-Gemcitabine and 5'-O-DMT-(N-bz) Gemcitabine prepared as above, were tested for their stability. The kinetics of 2'-deoxy, 2',2'-difluorocytidine when kept in pyridine and ammonia at 37° C. for 18 hrs, showed no breakdown of Gemcitabine, other than loss of the protecting group, as revealed by its TLC (thin layer chromatography), Rf value and UV data.

When N-Bz-2'-deoxy, 2',2'-difluorocytidine (Compound II) was treated under the above set of conditions for the hydrolysis of N-protecting group, it was converted into 2'-deoxy, 2',2'-difluorocytidine completely without any deterioration and byproduct formation, as shown by its TLC, Rf, UV, and HPLC data which matched with that of 2'-deoxy, 2',2'-difluorocytidine.

Example V

Preparation of dFC GG ACG (SEQ ID NO: 7)

Oligonucleotides were synthesized by the phosphoramidite method cited above according to the methods described in Genome Research 7:741-747 (1998) which is hereby incorporated by reference. Preparation of oligonucleotides of the invention was carried out following per se known method utilizing the MerMade IV synthesizer (sold by BioAutomation, Texas USA). (The protocol of oligo synthesis is provided by the instrument manufacturer, and is used as outlined in the chart below). A typical example of preparation is given below taking preparation of dFC GG ACG (dFC==2'-deoxy, 2',2'-difluorocytidine), as an example.

Preparation of the oligonucleotide dFC GG ACG (SEQ ID NO: 7)
Sequence: dFC GG ACG (SEQ ID NO: 7)
Synthesis scale: 10 μmole

| | # of Cycles | Reagent | Wait Time (sec) | Volume (μl) |
|---|---|---|---|---|
| Cycle 1 | | | | |
| Prewash | 2 | Synthesis Grade Acetonitrile | — | 350 |
| | | DNA Protocol | | |
| Cycle 2a | | | | |
| Deblock | 2 | 3% TCA/DCM | 20 | 150 |
| Wash | 3 | Synthesis Grade Acetonitrile | — | 350 |
| Coupling | 1 | DNA amidites (0.075M concentration) | 90 | 60 |
| Activator | 1 | 5-Ethylthio Tetrazole (0.44M) | | 120 |
| Wash | 1 | Synthesis Grade Acetonitrile | — | 350 |
| Cap A | 1 | Acetic anhydride/THF/Pyridine | 50 | 120 |
| Cap B | 1 | N-Methyl imidazole/THF | | 100 |
| Wash | 1 | Synthesis Grade Acetonitrile | — | 350 |
| Oxidize | 1 | 0.02M Iodine in Pyridine/THF/Water | 25 | 100 |
| Wash | 3 | Synthesis Grade Acetonitrile | — | 350 |

-continued

Preparation of the oligonucleotide dFC GG ACG (SEQ ID NO: 7)
Sequence: dFC GG ACG (SEQ ID NO: 7)
Synthesis scale: 10 μmole

| | # of Cycles | Reagent | Wait Time (sec) | Volume (μl) |
|---|---|---|---|---|
| | | Gemcitabine Protocol | | |
| Cycle 2b | | | | |
| Deblock | 2 | 3% TCA/DCM | 45 | 150 |
| Wash | 3 | Synthesis Grade Acetonitrile | — | 350 |
| Coupling | 1 | Gemcitabine amidite (0.075M concentration) | 100 | 60 |
| Activator | 3 | 5-Ethylthio Tetrazole (0.44M) | | 120 |
| Wash | 1 | Synthesis Grade Acetonitrile | — | 350 |
| Cap A | 1 | Acetic anhydride/THF/Pyridine | 50 | 120 |
| Cap B | 1 | N-Methyl imidazole/THF | | 100 |
| Wash | 1 | Synthesis Grade Acetonitrile | — | 350 |
| Oxidize | 1 | 0.02M Iodine in Pyridine/THF/Water | 80 | 100 |
| Wash | 3 | Synthesis Grade Acetonitrile | — | 350 |

Cycle 1 Successfully completed 1 time
Cycle2a Successfully completed 4 times
Cycle 2b Successfully completed 1 time The desired ODN (oligodeoxynucleotide) sequence dFC GG ACG (SEQ ID NO: 7 was obtained at 90.6% purity as shown by HPLC analysis data (FIGS. 5A-B).

Purification: Standard purification methods were followed using column chromatography and HPLC techniques.

Example VI

Quality Control Data

Purity of the products was confirmed by UV, HPLC, and Capillary Gel Electrophoresis (CE) methods.

The ultraviolet spectra of the monomers, the trityl values and the OD units of the oligomers were obtained on the Shimadzu UV-1201 Spectrophotometer. The $^{1}$H proton and $^{31}$p phosphorus nuclear magnetic resonance spectra were done by Nu Mega Resonance Labs, Inc., San Diego, Calif. The data were acquired on Bruker-AMX R-2, 500 MHz for 1H and 202 MHz for 31 P NMR. 1 H-NMR spectra were referenced to the internal CHCl$_3$ signal, and 1% TMS in the sample, 7.24 ppm and 0 ppm, respectively (Tables 1-3). 31 P-NMR chemical shifts listed are downfield from 85% H$_3$PO$_4$, externally referenced. All the spectra were run in CDCl$_3$ (Cambridge Isotopes). CDCl$_3$ was also used as a lock reference in 31 P-NMR analysis. DNA was synthesized on the MerMade 4 96 well synthesizer and Expedite model 8909. The sequences were synthesized with standard protocols for defined sequence DNA synthesis (0.2 micromole scale and 10 umole scale as provided in the protocol by the manufacturer of the synthesizers).

The HPLC analysis was done on the Varian 9300 instrument equipped with Prostar 210 delivery pumps for gradient runs of the samples, and Varian Prostar model 340 variable wavelength UV-VIS detector and data system for storage of data. The analysis was performed at 256 nm wavelength.

Chrompack HPLC columns, length 250 mm with omnisphere C18 packing were used for the analyses.

Thin layer chromatography (TLC) was carried out on Baker-Flex silica gel IB-F TLC plates (20×20 cm and 5×20 cm). Column Chromatography was carried out using silica gel 60 (EM Science), particle size 0.04-0.063 mm (230-400 mesh), and particle size 0.063-200 mm (70-230 mesh).

The capillary Gel analysis was performed on the Beckman Coulter Instrument model PACE MDQ, with UV detector. The detection was done at 254 nm. The capillary used in the system was 30 cm length from Beckman Coulter Instruments, and MDQ gel and buffer was used for sample analysis. The capillary gel is equilibrated in run buffer and applying 100 V/cm (3 kV) followed by 300 V/cm (9 kV) for 10 minutes). Multiple samples were analyzed simultaneously and stored on the MDQ data system.

HPLC was Performed as Follows:

Column: Hamilton PRP-1 (4.1×150 mm), P/N 79425

Detection: UV @ 260 nm, Sensitivity 0.002 AUFS

Mobile Phase: A: 0.1 M Triethyl ammonium acetate (pH 7.5) B: Acetonitrile Gradient:

0 min 5%B

Example VII

Flow Cytometric Evaluation of the DNA Cell Cycle Profile a. Cell Culture

Monolayer cultures of human colon adenocarcinoma cancerous cells HT29 (American Type Culture Collection HTB-38), and human colon normal cells CCD112CoN (American Type Culture Collection CRL-1541) were grown in DMEM growth medium, or Dulbecco's modified Eagle's medium (DMEM; Sigma Chemical Co., St. Louis, Mo.) containing 10% fetal bovine serum (FBS; Biological Industries, Kibbutz, Israel). Incubation was in 10% $CO_2$ at 37° C.

b. Gemcitabine (Gemzar) Versus Gemcitabine-Oligodeoxynucleotide (Gemzar-ODN) Dose-Response Gemzar (MW 299.5), or 2'-deoxy, 2',2'-difluorocytidine hydrochloride for injection, as manufactured by Lilly France S.A., Fegersheim, France). Gemzar-ODNs were 2'-deoxy, 2',2'-difluorocytidine (dFC, or difluorodeoxycitidine) linked to 4 oligodeoxynucleotide (ODN) sequences (synthesized by Chemgenes Corp, Wilmington, Mass.) as follows:

Aqueous stock solutions were prepared at the Gemzar or Gemzar-equivalent concentration of 0.2 mg/ml. Parallel monolayer cultures in log phase growth were treated for 1 hr at 37° C. with a final concentration of 0, 20 and 50 ng/ml of Gemzar or Gemzar equivalent from each of the 4 sequences of Gemzar-ODN that were synthesized. After the 1 hr pulse treatment with either Gemzar or Gemzar-ODNs, the cell cultures were reincubated for another 47 hr at 37° C. in normal DMEM growth medium without Gemzar or Gemzar-ODN. Control cultures were similar parallel cultures and had similar 1 hr and 47 hr reincubations, except without any Gemzar or Gemzar-ODN content. After the 47 hr reincubation, all cultures were evaluated at the same time for their DNA cell cycle profile using flow cytometry.

c. Flow Cytometric Evaluation of DNA Cell Cycle Profile

This was evaluated as previously described (Cell Death Differ. 4: 213-223, 1997; Exp. Cell Res. 240: 293-304, 1998). Propidium iodide (PI) stock solution was prepared at 50 ug/ml in tris buffered saline (1.21 mg/ml Tris, 0.584 mg/ml NaCl). Ribonuclease A (RNase A) was freshly added to the PI stock solution at 6 mg/ml immediately before use. Cells were harvested by scraping with a cell scraper and triturated to obtain a single cell suspension using a hypodermic syringe fitted with a 21-gauge needle. Cells were spun down at 1000 g for 5 min, and washed once in 5 ml phosphate buffered saline (PBS A, Oxoid, London, UK). Cells were then permeabilized by resuspending in 1% Bouin's fluid (15 parts 1.2% saturated aqueous picric acid, 5 parts formalin, 1 part glacial acetic acid) in PBS. Cells were repelleted and suspend in the PI-RNase for 1 hour over ice, before flow cytometric evaluation at ex/em 488/590 nm and 20,000 counts sample size. The Coulter Epics Elite ESP flow cytometer and Workstation program version 4.01 (Coulter Electronics, Hialeah, Fla.) were used with WinMDI version 2.8 (Scripps Research Institute, La Jolla, Calif.

FIG. 13 shows flow cytometric DNA cell cycle profiles showing 2'-deoxy, 2',2'-difluorocytidine-ODNs killing colon cancerous cells HT29 much more effectively than by treatment with Gemzar alone, at equivalent dosages. Cells were treated in culture with respective drugs for 1 hour at the stated dosage, and reincubated in normal medium without drugs for a further 47 hours. Column A is treatment by Gemzar alone. Column B-E are treatments by 2'-deoxy, 2',2'-difluorocytidine-ODN sequence 7-10, at equivalent Gemzar dosages.

| DESIGNATION | GEMZAR-ODN (dFC = 2'-deoxy 2',2' difluorocytidine hydrochloride) | MW | Quantity supplied | Gemzar equivalent |
|---|---|---|---|---|
| SEQ ID NO: 7 | dFC GGA CG | 1852.27 | 4002 nmole | 193,805 μg |
| SEQ ID NO: 8 | dFC GTG AAA CG | 2798.87 | 5134 nmole | 164,538 μg |
| SEQ ID NO: 9 | dFC GGA CGT GGA ACG | 4059.67 | 820 nmole | 11,489 μg |
| SEQ ID NO: 10 | dFC GGA GCT GGA ACG | 4059.67 | 3450 nanomole | 76,299 μg |

| DESIGNATION | GEMZAR-OLIGOS (dfC = GEMZAR) | MW | Quantity synthesized |
|---|---|---|---|
| SEQ ID NO: 7 | dFC GGA CG | 1852.27 | 233 OD = 4002 nmole |
| SEQ ID NO: 8 | dFC GTG AAA CG | 2798.87 | 457 OD = 5134 nmole |
| SEQ ID NO: 9 | dFC GGA CGT GGA ACG | 4059.67 | 106 OD = 820 nmole |
| SEQ ID NO: 10 | dFC GGA GCT GGA ACG | 4059.67 | 442 OD = 3450 nmole |

In particular. FIG. 13 (and FIG. 14 described below) show data for the following:

| POSITION IN FIGURE | DATA FOR |
|---|---|
| I(A) | Control |
| II(A) | 20ng/ml Gemzar |
| II(B) | 20ng/ml Gemzar equivalent SEQ ID NO:7 |
| II(C) | 20ng/ml Gemzar equivalent SEQ ID NO:8 |
| II(D) | 20ng/ml Gemzar equivalent SEQ ID NO:9 |
| II(E) | 20ng/ml Gemzar equivalent SEQ ID NO:10 |
| III(A) | 50ng/ml Gemzar |
| III(B) | 50ng/ml Gemzar equivalent SEQ ID NO:7 |
| III(C) | 50ng/ml Gemzar equivalent SEQ ID NO:8 |
| III(D) | 50ng/ml Gemzar equivalent SEQ ID NO:9 |
| III(E) | 50ng/ml Gemzar equivalent SEQ ID NO:10 |

FIG. 14 shows flow cytometric DNA cell cycle profiles showing 2'-deoxy, 2',2'-difluorocytidine-ODNs killing colon normal cells CCD-112CO more effectively than by treatment with Gemzar alone, at equivalent dosages. Cells were treated in culture with respective drugs for 1 hour at the stated dosage, and reincubated in normal medium without drugs for a further 47 hours. Column A is treatment by Gemzar alone. Column B-E are treatments by 2'-deoxy, 2',2'-difluorocytidine-ODN sequences 7-10, at equivalent Gemzar dosages, similar to those used in colon cancerous cells HT29 shown above in FIG. 13.

Comparing column A of FIG. 13 with column A of FIG. 14, it is clear that there is only minimal difference between the killing of cancer and normal cells by Gemzar alone. Comparing columns B-E of FIG. 13 with columns B-E of FIG. 14, it is clear that 2'-deoxy, 2',2'-difluorocytidine-ODNs of sequences 1-4 are more effective in killing cancerous cells than normal cells at equivalent dosages. The details of the method of flow cytometry have been described previously (L. Qi and K. H. Sit; Mol. Cell Biol. Res. Comms., 3: 33-41, 2000; L. Qi and K. H. Sit; Mol. Cell Biol. Res. Comms., 3: 319-327, 2000; D. L. Chen, M. Swe, K. H. Sit; Exp. Cell Res., 240: 293-303, 1998). Each of these references is hereby incorporated by reference.

Example VIII

Testing of Oligonucleotides and Compositions of the Inventions for Biological Activity in Human Oligonucleotides comprising a prodrug of the invention are tested for efficacy in humans using published methods, such as those described in Cancer Invest. 21(5): 690-4, 2003, or Lung Cancer. October 42(1): 97-102, 2003. The oligonucleotides comprising the prodrug are administered in pharmaceutical compositions as taught herein and further as well known to the skilled artisan.

What we claim is:

1. A synthetic oligonucleotide for preferentially killing cancerous cells over noncancerous cells comprising at least two CpG moieties and a covalently linked nucleoside antimetabolite.

2. A synthetic oligonucleotide for preferentially killing cancerous cells over noncancerous cells comprising at least two CpG moieties and a covalently linked nucleoside antimetabolite, wherein, the antimetabolite is selected from the group consisting of 2'-deoxy-3'-thiacytidine, 3'-azido-3'-deoxythymidine, 2',3'-dideoxycytidine, 2',3'-didehydro-3'-deoxythymidine, 2',3'-dideoxyinosine, 5-fluoro-2'-deoxy uridine, 2-fluoro-9-b-D-arabinofuranosyladenine, 1-B-D-arabinofuranosylcytosine, 5-azacytidine, 5-aza-2'-deoxycytidine, 6-mercaptopurineriboside, 2-chlorodeoxyadenosine, pentostatin and 2'-deoxy, 2',2'-difluorocytidine.

3. The oligonucleotide of claim 1 or 2, wherein two of said at least two CpG moieties are separated by a number of nucleotides selected from the group of numbers 2, 5, and 9.

4. The oligonucleotide of claim 1 or 2, wherein said nucleoside antimetabolite is 5' to said at least two CpG moieties.

5. The oligonucleotide of claim 1 or 2, wherein said nucleoside antimetabolite is 3' to said at least two CpG moieties.

6. The oligonucleotide of claim 1 or 2, wherein said nucleoside antimetabolite is 3' to at least one of said at least two CpG moieties and 5' to at least a second of said at least two CpG moieties.

7. The oligonucleotide of claim 1 or 2, wherein said nucleoside antimetabolite is linked by a 3'-3' linkage.

8. The oligonucleotide of claim 1 or 2, wherein said nucleoside antimetabolite is linked by a 5'-5' linkage.

9. The oligonucleotide of claim 1 or 2, wherein said nucleoside antimetabolite is linked by a 3'-5' linkage.

10. The oligonucleotide of claim 1 or 2, wherein said nucleoside antimetabolite is linked by a 5'-3' linkage.

11. The oligonucleotide of claim 1 or 2, wherein said nucleoside antimetabolite is linked at a position that is selected from the following positions: 10 nucleotides upstream from one of the said at least two CpG moieties, 9 nucleotides upstream from one of the said at least two CpG moieties, 8 nucleotides upstream from one of the said at least two CpG moieties, 7 nucleotides upstream from one of the said at least two CpG moieties, 6 nucleotides upstream from one of the said at least two CpG moieties, 5 nucleotides upstream from one of the said at least two CpG moieties, 4 nucleotides upstream from one of the said at least two CpG moieties, 3 nucleotides upstream from one of the said at least two CpG moieties, 2 nucleotides upstream from one of the said at least two CpG moieties, 1 nucleotides upstream from one of the said at least two CpG moieties, 10 nucleotides downstream from CpG moieties, 9 nucleotides downstream from one of the said at least two CpG moieties, 8 nucleotides downstream from one of the said at least two CpG moieties, 7 nucleotides downstream from one of the said at least two CpG moieties, 6 nucleotides downstream from one of the said at least two CpG moieties, 5 nucleotides downstream from one of the said at least two CpG moieties, 4 nucleotides downstream from one of the said at least two CpG moieties, 3 nucleotides downstream from one of the said at least two CpG moieties, 2 nucleotides downstream from one of the said at least two CpG moieties, and 1 nucleotides downstream from one of the said at least two CpG moieties.

12. The oligonucleotide of claim 1 or 2, wherein the nucleoside antimetabolite is linked by a linker having the formula

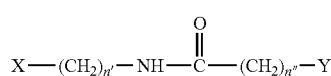

wherein X and Y are independently selected from

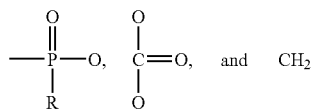

and R is selected from the group consisting of H, S, $C_1$-C6 alkyl, $C_1$-C6 alkoxy, and NH.

13. The oligonucleotide of claim 1 or 2, wherein the oligonucleotide comprises at least one nucleotide having a ribose sugar moiety.

14. The oligonucleotide of claim 1 or 2, wherein the oligonucleotide comprises at least one nucleotide having a 2'-deoxyribose sugar moiety.

15. The oligonucleotide of claim 1 or 2, wherein the oligonucleotide comprises at least one 2'-halogen nucleotide.

16. The oligonucleotide of claim 1 or 2, comprising at least one 2'-N-alkyl nucleotide, wherein the alkyl has between 1 and 6 carbon atoms.

17. The oligonucleotide of claim 1 or 2, comprising at least one 2'-O-alkyl nucleotide, 2'-n-alkyl nucleotide, or 2'-O-halogen nucleotide, wherein an alkyl has between 1 and 6 carbon atoms.

18. The oligonucleotide of claim 17, wherein each alkyl is methyl.

19. The oligonucleotide of claim 1 or 2, comprising a plurality of nucleotides connected by covalent internucleotide linkages selected from the group consisting of phosphodiester linkage, C1-C6 alkoxy phosphotriester linkage, phosphorothioate linkage and phosphoramidate linkage.

20. A pharmaceutical composition comprising the oligonucleotide of any of claims 1 or 2-19.

21. A pharmaceutical composition of claim 20 further comprising a pharmaceutically acceptable carrier.

22. The oligonucleotide of claim 21 wherein said pharmaceutically acceptable carrier is lipofectin.

23. A synthetic oligonucleotide for preferentially killing cancerous cells over noncancerous cells comprising a motif represented by one of the group of formulas 5'-PCGXCG-3' and 5'-CGXCGP-3', wherein P is a nucleoside antimetabolite and X represents between 0 and 50 nucleotides.

24. A synthetic oligonucleotide for preferentially killing cancerous cells over noncancerous cells comprising a motif represented by one of the group of formulas 5'-PCGXCG-3' and 5'-CGXCGP-3', and wherein X represents between 0 and 50 nucleotides and P is a nucleoside antimetabolite selected from the group consisting of 2'-deoxy-3'-thiacytidine, 3'-azido-3'-deoxythymidine, 2',3'-dideoxycytidine, 2',3'-didehydro-3'-deoxythymidine, 2',3'-dideoxyinosine, 5-fluoro-2'-deoxy uridine, 2-fluoro-9-b-D-arabinofuranosyladenine, 1-B-D-arabinofuranosylcytosine, 5-azacytidine, 5-aza-2'-deoxycytidine, 6-mercaptopurineriboside, 2-chlorodeoxyadenosine, pentostatin and 2'-deoxy, 2'-,2'-difluorocytidine.

25. The oligonucleotide of claim of 23 or 24, where X is selected from the group consisting of 2, 5, and 9 nucleotides.

26. The oligonucleotide of claim 23 or 24, wherein X has at least one nucleotide and the nucleoside antimetabolite is covalently linked to one of the nucleotides by a 3'-3' linkage.

27. The oligonucleotide of claim 23 or 24, wherein X has at least one nucleotide and the nucleoside antimetabolite is covalently linked to one of the nucleotides by a 5'-5' linkage.

28. The oligonucleotide of claim 23 or 24, wherein X has at least one nucleotide and the nucleoside antimetabolite is covalently linked to one of the nucleotides by a 3'-5' linkage.

29. The oligonucleotide of claim 23 or 24, wherein X has at least one nucleotide and the nucleoside antimetabolite is covalently linked to one of the nucleotides by a 5'-3' linkage.

30. The oligonucleotide of claim 23 or 24, comprising at least one nucleotide having a ribose sugar moiety.

31. The oligonucleotide of claim 23 or 24, comprising at least one nucleotide having a 2'-deoxyribose sugar moiety.

32. The oligonucleotide of claim 23 or 24, comprising at least one 2'-O-alkyl nucleotide, 2'-N-Alkyl nucleotide, or 2'-O-halogen nucleotide, wherein an alkyl has between 1 and 6 carbon atoms.

33. The oligonucleotide of claim 23 or 24, comprising a plurality of nucleotides connected by covalent internucleoside linkages, wherein the linkages are selected from the group consisting of phosphodiester linkage, C1-C6 alkoxy phosphotriester linkage, phosphorothioate linkage and phosphoramidate linkage.

34. The oligonucleotide of claim 23 or 24, wherein X has at least one nucleotide and the nucleoside antimetabolite is attached to at least one of the multiple nucleotides by a linker having the formula

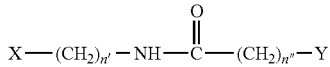

wherein X and Y are independently selected from

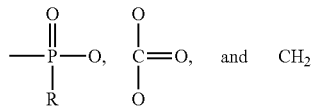

and R is selected from the group consisting of H, S, $C_1$-C6 alkyl, $C_1$-C6 alkoxy, and NH.

35. A pharmaceutical composition comprising the oligonucleotide of any of claims 23-34.

36. A pharmaceutical composition of claim 35 further comprising a pharmaceutically acceptable carrier.

37. The oligonucleotide of claim 36 wherein said pharmaceutically acceptable carrier is lipofectin.

38. A method of synthesizing an oligonucleotide product for preferentially killing cancerous cells over non-cancerous cells comprising the steps of:
(a) Selecting a oligonucleotide comprising at least two CpG moieties; and
(b) Covalently linking a nucleoside antimetabolite to said oligonucleotide comprising at least two CpG moieties.

39. A method of synthesizing an oligonucleotide product for preferentially killing cancerous cells over non-cancerous cells comprising the steps of:
(a) Selecting a oligonucleotide comprising at least two CpG moieties; and
(b) Covalently linking a nucleoside antimetabolite to said oligonucleotide comprising at least two CpG moieties, wherein, said antimetabolite is selected from the group consisting of 2'-deoxy-3'-thiacytidine, 3'-azido-3'-deoxythymidine, 2',3'-dideoxycytidine, 2',3'-didehydro-3'-deoxythymidine, 2',3'-dideoxyinosine, 5-fluoro-2'-deoxy uridine, 2-fluoro-9-b-D-arabinofuranosyladenine, 1-B-D-arabinofuranosylcytosine, 5-azacytidine, 5-aza-2'-deoxycytidine, 6-mercaptopurineriboside, 2-chlorodeoxyadenosine, pentostatin and 2'-deoxy, 2',2'-difluorocytidine.

40. The method of claim 38 or 39, wherein said oligonucleotide comprising at least two CpG moieties comprises between 2 and 50 nucleotides.

* * * * *

SEQUENCE LISTING

<160> NUMBER OF SEQ ID NOS: 10

<210> SEQ ID NO 1
<211> LENGTH: 13
<212> TYPE: DNA
<213> ORGANISM: Homo sapiens
<220> FEATURE:
<221> NAME/KEY: misc_feature
<222> LOCATION: (3)..(11)
<223> OTHER INFORMATION: Each n represents any nucleotide. n's may be identical or different from each other.

<400> SEQUENCE: 1
gcnnnnnnnn ngc                                              13

<210> SEQ ID NO 2
<211> LENGTH: 5
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n represents any nucleotide.

```
<400> SEQUENCE: 2 gcngc                                                              5

<210> SEQ ID NO 3
<211> LENGTH: 5
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n represents any nucleotide.

<400> SEQUENCE: 3 cgncg                                                              5

<210> SEQ ID NO 4
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Each n represents any nucleotide. n's may be
      identical or different from each other.

<400> SEQUENCE: 4 gcnngc                                                             6

<210> SEQ ID NO 5
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Each n represents any nucleotide, and the n's
      may be identical or different from each other.

<400> SEQUENCE: 5 gcnnnngc                                                           8

<210> SEQ ID NO 6
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(11)
<223> OTHER INFORMATION: Each n represents any nucleotide.

<400> SEQUENCE: 6 gcnnnnnnn ngc                                                      13

<210> SEQ ID NO 7
<211> LENGTH: 6
<212> TYPE: DNA
<213> ORGANISM: Artificial Sequence
<220> FEATURE:
<223> OTHER INFORMATION: Synthetic
<220> FEATURE:
```

```
-continued

<221> NAME/KEY: modified_base
<222> LOCATION: (1)..(1)
<223> OTHER INFORMATION: n represents 2'-deoxy, 2'-2'-difluorocytidine
      or a, c, g, or t

<400> SEQUENCE: 7 nggacg                                                                  6

<210> SEQ ID NO 8
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: n represents 2'-deoxy, 2'-2'-difluorocytidine
      or a, c, g, or t

<400> SEQUENCE: 8 ngtggaacg                                                               9

<210> SEQ ID NO 9
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: n represents 2'-deoxy, 2'-2'-difluorocytidine
      or a, c, g, or t

<400> SEQUENCE: 9
nggacgtgga acg                                                         13

<210> SEQ ID NO 10
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n represents 2'-deoxy, 2'-2'-difluorocytidine

<400> SEQUENCE: 10
nggagctgga acg                                                         13
```